United States Patent
Baker et al.

(10) Patent No.: US 11,960,264 B2
(45) Date of Patent: Apr. 16, 2024

(54) LOAD CONTROL SYSTEM RESPONSIVE TO SENSORS AND MOBILE DEVICES

(71) Applicant: Lutron Technology Company LLC, Coopersburg, PA (US)

(72) Inventors: Rhodes B. Baker, Bethlehem, PA (US); Jason C. Killo, Emmaus, PA (US); Galen Edgar Knode, Macungie, PA (US); Sanjeev Kumar, Harleysville, PA (US); Brent Protzman, Easton, PA (US); Daniel Curtis Raneri, Orefield, PA (US); Greg Edward Sloan, Allentown, PA (US)

(73) Assignee: Lutron Technology Company LLC, Coopersburg, PA (US)

(*) Notice: Subject to any disclaimer, the term of this patent is extended or adjusted under 35 U.S.C. 154(b) by 289 days.

(21) Appl. No.: 17/474,092

(22) Filed: Sep. 14, 2021

(65) Prior Publication Data

US 2021/0410253 A1 Dec. 30, 2021

Related U.S. Application Data

(63) Continuation of application No. 14/832,727, filed on Aug. 21, 2015, now abandoned.
(Continued)

(51) Int. Cl.
| | |
|---|---|
| *G05B 19/048* | (2006.01) |
| *A61M 21/00* | (2006.01) |

(Continued)

(52) U.S. Cl.
CPC ........... *G05B 19/048* (2013.01); *A61M 21/00* (2013.01); *A61N 5/0618* (2013.01); *E04F 19/00* (2013.01);
(Continued)

(58) Field of Classification Search
CPC .............. G05B 19/048; G05B 15/02; G05B 2219/2642; A61M 21/00; A61M 16/161;
(Continued)

(56) References Cited

U.S. PATENT DOCUMENTS

| | | |
|---|---|---|
| 5,248,919 A | 9/1993 | Hanna et al. |
| 7,391,297 B2 | 6/2008 | Cash et al. |

(Continued)

FOREIGN PATENT DOCUMENTS

| | | |
|---|---|---|
| CN | 102293058 A | 12/2011 |
| CN | 102833910 A | 12/2012 |

(Continued)

OTHER PUBLICATIONS

Estel, et al., Feasibility of Bluetooth iBeacons for Indoor Localization, 2015, 12 pages.
English translation: KR 2009-0106149.

*Primary Examiner* — Richard Tan
(74) *Attorney, Agent, or Firm* — Michael S. Czarnecki; Glen R. Farbanish; Philip N. Smith

(57) ABSTRACT

A load control system may control an electrical load in a space of a building based on one or more parameters regarding the physical condition of an occupant. The parameters may be gathered by one or more sensing devices. The sensing devices may be included in a mobile device. A system controller may receive the parameters and may automatically control the electrical loads in response to the parameters. The system controller may control the electrical load to attempt to adjust the physical condition of the occupant in response to the sensed parameters. The system controller may control the electrical load to provide an alert, an alarm, and/or a warning in response to the sensed parameters.

33 Claims, 9 Drawing Sheets

Related U.S. Application Data

(60) Provisional application No. 62/094,429, filed on Dec. 19, 2014, provisional application No. 62/040,848, filed on Aug. 22, 2014.

(51) Int. Cl.

| | | |
|---|---|---|
| *A61N 5/06* | (2006.01) | |
| *E04F 19/00* | (2006.01) | |
| *E06B 9/24* | (2006.01) | |
| *F24F 11/30* | (2018.01) | |
| *F24F 11/46* | (2018.01) | |
| *F24F 11/64* | (2018.01) | |
| *G05B 15/02* | (2006.01) | |
| *G08B 21/18* | (2006.01) | |
| *H02J 4/00* | (2006.01) | |
| *H05B 45/18* | (2020.01) | |
| *H05B 47/11* | (2020.01) | |
| *H05B 47/115* | (2020.01) | |
| *A61M 16/16* | (2006.01) | |
| *F24F 120/10* | (2018.01) | |
| *F24F 120/12* | (2018.01) | |
| *F24F 120/14* | (2018.01) | |

(52) U.S. Cl.
CPC .............. *E06B 9/24* (2013.01); *F24F 11/30* (2018.01); *F24F 11/46* (2018.01); *F24F 11/64* (2018.01); *G05B 15/02* (2013.01); *G08B 21/185* (2013.01); *H02J 4/00* (2013.01); *H05B 45/18* (2020.01); *H05B 47/11* (2020.01); *H05B 47/115* (2020.01); *A61M 16/161* (2014.02); *A61M 2021/0044* (2013.01); *A61M 2021/0066* (2013.01); *A61M 2202/0233* (2013.01); *A61M 2205/33* (2013.01); *A61M 2205/3306* (2013.01); *A61M 2205/3344* (2013.01); *A61M 2205/3368* (2013.01); *A61M 2205/3569* (2013.01); *A61M 2205/3592* (2013.01); *A61M 2205/505* (2013.01); *A61M 2205/8206* (2013.01); *A61M 2230/06* (2013.01); *A61M 2230/201* (2013.01); *A61M 2230/30* (2013.01); *A61M 2230/50* (2013.01); *A61N 2005/0626* (2013.01); *A61N 2005/0636* (2013.01); *E06B 2009/247* (2013.01); *F24F 2120/10* (2018.01); *F24F 2120/12* (2018.01); *F24F 2120/14* (2018.01); *G05B 2219/2642* (2013.01)

(58) Field of Classification Search
CPC .. A61M 2021/0044; A61M 2021/0066; A61M 2202/0233; A61M 2205/33; A61M 2205/3306; A61M 2205/3344; A61M 2205/3368; A61M 2205/3569; A61M 2205/3592; A61M 2205/505; A61M 2205/8206; A61M 2230/06; A61M 2230/201; A61M 2230/30; A61M 2230/50; A61N 5/0618; A61N 2005/0626; A61N 2005/0636; E04F 19/00; E06B 9/24; E06B 2009/247; F24F 11/30; F24F 11/46; F24F 11/64; F24F 2120/10; F24F 2120/12; F24F 2120/14; G08B 21/185; H02J 4/00; H05B 45/18; H05B 47/11; H05B 47/115; Y02B 20/40

USPC .......................................................... 307/31
See application file for complete search history.

(56) References Cited

U.S. PATENT DOCUMENTS

| | | |
|---|---|---|
| 7,925,384 B2 | 4/2011 | Huizenga et al. |
| 8,009,042 B2 | 8/2011 | Steiner et al. |
| 8,199,010 B2 | 6/2012 | Sloan et al. |
| 8,228,184 B2 | 7/2012 | Blakeley et al. |
| 8,410,706 B2 | 4/2013 | Steiner et al. |
| 8,451,116 B2 | 5/2013 | Steiner et al. |
| 8,570,221 B2 | 10/2013 | Bao et al. |
| 8,659,230 B2 | 2/2014 | Nanahara et al. |
| 8,665,090 B2 | 3/2014 | Bull |
| 9,232,610 B2 | 1/2016 | Gritti |
| 9,237,620 B1 | 1/2016 | Knapp et al. |
| 9,345,115 B2 | 5/2016 | Mohan |
| 9,386,668 B2 | 7/2016 | Knapp et al. |
| 9,578,724 B1 | 2/2017 | Knapp et al. |
| 9,651,632 B1 | 5/2017 | Knapp et al. |
| 2003/0098133 A1 | 5/2003 | Palmer |
| 2005/0131554 A1 | 6/2005 | Bamberger et al. |
| 2008/0092075 A1 | 4/2008 | Jacob et al. |
| 2009/0206983 A1 | 8/2009 | Knode et al. |
| 2010/0245588 A1 | 9/2010 | Waehner et al. |
| 2011/0257466 A1 | 10/2011 | Pintert et al. |
| 2012/0001567 A1 | 1/2012 | Knapp et al. |
| 2013/0030589 A1 | 1/2013 | Pessina et al. |
| 2014/0031987 A1 | 1/2014 | Ericsson et al. |
| 2014/0132475 A1 | 5/2014 | Bhutani et al. |
| 2014/0207292 A1 | 7/2014 | Ramagem et al. |
| 2014/0235269 A1 | 8/2014 | Ericsson et al. |
| 2014/0265568 A1 | 9/2014 | Crafts et al. |
| 2014/0312777 A1 | 10/2014 | Shearer et al. |
| 2015/0189068 A1 | 7/2015 | Mohan et al. |
| 2015/0228419 A1 | 8/2015 | Fadell et al. |
| 2018/0032043 A1 | 2/2018 | Matsuoka et al. |

FOREIGN PATENT DOCUMENTS

| | | | |
|---|---|---|---|
| EP | 2934071 A1 | | 10/2015 |
| KR | 1020090106149 A | | 10/2009 |
| WO | 1999056262 A1 | | 11/1999 |
| WO | WO2007030322 | * | 3/2007 |
| WO | 2012146256 A2 | | 4/2012 |
| WO | WO2012146256 | * | 11/2012 |

\* cited by examiner

LOAD CONTROL SYSTEM RESPONSIVE TO SENSORS AND MOBILE DEVICES

CROSS-REFERENCE TO RELATED APPLICATIONS

This application is a continuation of U.S. patent application Ser. No. 14/832,727 filed Aug. 21, 2015; which claims the benefit of U.S. Provisional Application No. 62/040,848, filed Aug. 22, 2014, and U.S. Provisional Application No. 62/094,429, filed Dec. 19, 2014, all of which are incorporated by reference herein as if fully set forth.

BACKGROUND

A user environment, such as a residence or an office building for example, may be configured using various types of load control systems. A lighting control system may be used to control the lighting loads in the user environment. A motorized window treatment control system may be used to control the natural light provided to the user environment. An HVAC system may be used to control the temperature in the user environment. Each load control system may include various control devices, including control-source devices and control-target devices. The control-target devices may receive digital messages, which may include load control instructions, for controlling an electrical load from one or more of the control-source devices. The control-target devices may be capable of directly controlling an electrical load. The control-source devices may be capable of indirectly controlling the electrical load via the control-target device. Examples of control-target devices may include lighting control devices (e.g., a dimmer switch, an electronic switch, a ballast, or a light-emitting diode (LED) driver), a motorized window treatment, a temperature control device (e.g., a thermostat), an AC plug-in load control device, and/or the like. Examples of control-source devices may include remote control devices, occupancy sensors, daylight sensors, temperature sensors, and/or the like.

Though current load control systems enable control of different electrical loads in a load control environment, the load control systems fail to use information that may be collected from one or more occupants and/or the occupant's mobile devices to control the electrical loads. Using such information may enable the load control systems to be more perceptive and to more conveniently control the electrical loads throughout the system.

SUMMARY

The present disclosure relates to a load control system for controlling the amount of power delivered to one or more electrical load, and more particularly, to a load control system able to control a plurality of electrical loads in response to detected information about one or more occupants in a space, such as a building. For example, information may be gathered about an occupant from one or more sensors, wearable wireless devices, or other devices.

As described herein, a load control system for controlling an electrical load in a space of a building occupied by an occupant may comprise a system controller and one or more load control devices. The load control system may include a mobile device that may be used for controlling the one or more load control devices. The mobile device may be a mobile phone, a wearable device, or other computing device, for example. The load control system may include one or more sensors or sensing devices for collecting information. For example, the mobile device may comprise one or more sensing devices for sensing one or more parameters regarding the physical condition of the occupant.

The system controller may receive sensor information that includes parameters that indicate a physical condition of the occupant. The system controller may determine load control instructions for controlling a load control device in response to the parameters that indicate the physical condition of the occupant. The system controller may send a digital message including the load control instructions to the load control device to automatically control the respective electrical load of the load control device in response to the sensed parameters.

The parameters may indicate that the occupant fell asleep, that the occupant is waking up, that an occupant's stress level is changing, that the occupant is moving, biometrics of the occupant, and/or other parameters that may indicate the physical condition of the occupant. The system controller may control the electrical loads in response to the parameters. For example, the system controller may automatically transmit digital messages that include instructions for controlling the electrical loads based on the parameters.

The system controller may control the respective electrical load of the load control device to attempt to adjust the physical condition of the occupant in response to the sensed parameters. The system controller may control the electrical load to provide an alert, an alarm, or a warning in response to the sensed parameters. The system controller may adjust a color temperature of the lighting load, adjust an amount of daylight allowed by a motorized window treatment, adjust a temperature of a temperature control device, and/or otherwise control an electrical load in response to the parameters that indicate the physical condition of the occupant.

Other features and advantages of the present disclosure will become apparent from the following detailed description that refers to the accompanying drawings.

DETAILED DESCRIPTION

Figure 1:
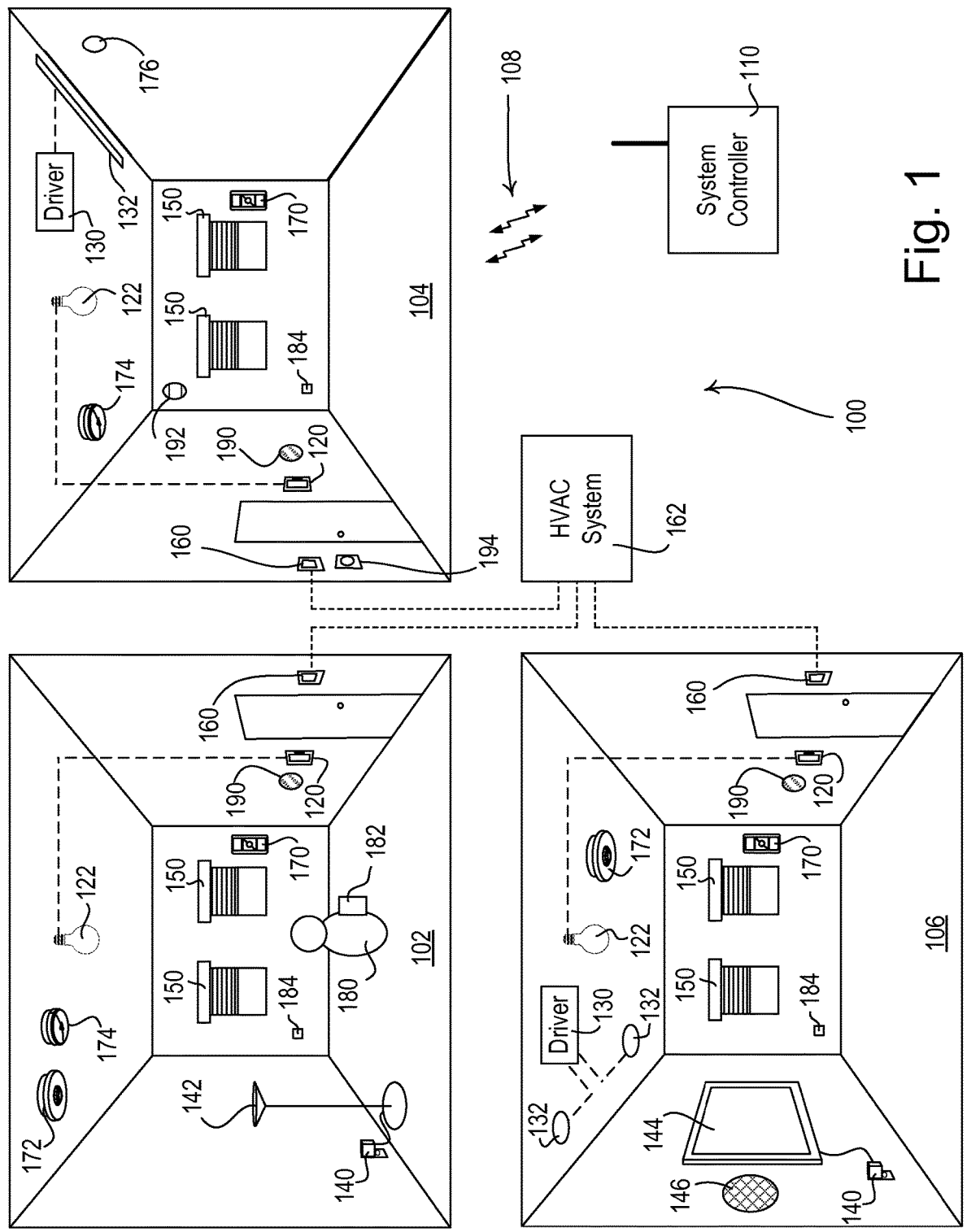
FIG. 1 is a diagram of an example load control system for controlling one or more electrical loads.

FIG. 1 is a diagram of an example load control system 100 for controlling the amount of power delivered from an alternating-current (AC) power source (not shown) to one or more electrical loads. The load control system 100 may be installed in a building having one or more rooms 102, 104, 106. The load control system 100 may comprise a plurality of control devices configured to communicate with each other via wireless signals, e.g., radio-frequency (RF) signals 108. Alternatively or additionally, the load control system 100 may comprise a wired digital communication link coupled to one or more of the control devices to provide for communication between the load control devices. The control devices of the load control system 100 may comprise a number of control-source devices (e.g., input devices operable to transmit digital messages in response to user inputs, occupancy/vacancy conditions, changes in measured light intensity, etc.) and a number of control-target devices (e.g., load control devices operable to receive digital messages and control respective electrical loads in response to the received digital messages). A single control device of the load control system 100 may operate as a control-source device and/or a control-target device (e.g., as both a control-source and a control-target device).

The control-source devices may be configured to transmit digital messages directly to the control-target devices. The load control system 100 may comprise a system controller 110 (e.g., a central controller or load controller) operable to communicate digital messages to and from the control devices (e.g., the control-source devices and/or the control-target devices). For example, the system controller 110 may be configured to receive digital messages from the control-source devices and transmit digital messages to the control-target devices in response to the digital messages received from the control-source devices. The digital messages transmitted to the control-target devices may include instructions generated for controlling a respective electrical load. The control-source and control-target devices and the system controller 110 may be configured to transmit and receive the RF signals 108 using a proprietary RF protocol, such as the ClearConnect® protocol. Alternatively, the RF signals 108 may be transmitted using a different RF protocol, such as, a standard protocol, for example, one of WIFI, ZIGBEE, Z-WAVE, KNX-RF, ENOCEAN RADIO protocols, or a different proprietary protocol.

The load control system 100 may comprise one or more load control devices, e.g., dimmer switches 120, for controlling respective lighting loads 122 located in one or more of the rooms 102, 104, 106. A dimmer switch 120 may be adapted to be wall-mounted in a standard electrical wallbox. The dimmer switch 120 may comprise a tabletop or plug-in load control device. The dimmer switch 120 may comprise a toggle actuator (e.g., a button) and an intensity adjustment actuator (e.g., a rocker switch). Actuations (e.g., successive actuations) of the toggle actuator may toggle, i.e., turn off and on, the respective lighting load 122. Actuations of an upper portion or a lower portion of the intensity adjustment actuator may respectively increase or decrease the amount of power delivered to the respective lighting load 122 and thus increase or decrease the intensity of the respective lighting load from a minimum intensity (e.g., approximately 1%) to a maximum intensity (e.g., approximately 100%). The dimmer switch 120 may comprise a plurality of visual indicators, e.g., light-emitting diodes (LEDs), which are arranged in a linear array and are illuminated to provide feedback of the intensity of the respective lighting load 122. Examples of wall-mounted dimmer switches are described in greater detail in U.S. Pat. No. 5,248,919, issued Sep. 29, 1993, entitled LIGHTING CONTROL DEVICE, and U.S. Patent Application Publication No. 2014/0132475, published May 15, 2014, entitled WIRELESS LOAD CONTROL DEVICE, the entire disclosures of which are hereby incorporated by reference.

The dimmer switch 120 may be configured to wirelessly receive digital messages via the RF signals 108 (e.g., from the system controller 110) and to control the respective lighting load 122 in response to the received digital messages. Examples of dimmer switches operable to transmit and receive digital messages is described in greater detail in commonly-assigned U.S. Patent Application Publication No. 2009/0206983, published Aug. 20, 2009, entitled COMMUNICATION PROTOCOL FOR A RADIO-FREQUENCY LOAD CONTROL SYSTEM, the entire disclosure of which is hereby incorporated by reference.

The load control system 100 may comprise one or more remotely-located load control devices, such as light-emitting diode (LED) drivers 130 for driving respective LED light sources 132 (e.g., LED light engines). The LED drivers 130 may be located remotely, for example, in or adjacent to the lighting fixtures of the respective LED light sources 132. The LED drivers 130 may be configured to receive digital messages via the RF signals 108 (e.g., from the system controller 110) and to control the respective LED light sources 132 in response to the received digital messages. The LED drivers 130 may be configured to adjust the color temperature of the respective LED light sources 132 in response to the received digital messages. Examples of LED drivers configured to control the color temperature of LED light sources are described in greater detail in commonly-assigned U.S. Patent Application Publication No. 2014/0312777, published Oct. 23, 2014, entitled SYSTEMS AND METHODS FOR CONTROLLING COLOR TEMPERATURE, the entire disclosure of which is hereby incorporated by reference. The load control system 100 may comprise other types of remotely-located load control devices, such as, for example, electronic dimming ballasts for driving fluorescent lamps.

The load control system 100 may comprise one or more plug-in load control devices 140 for controlling respective plug-in electrical loads. For example, a plug-in lighting load, such as a floor lamp 142 or a table lamp, may be plugged into one of the plug-in load control devices 140, such that the plug-in load control device is coupled in series between the AC power source and the plug-in lighting load. The plug-in load control device 140 may be configured to receive digital messages via the RF signals 108 (e.g., from the system controller 110) and to turn on and off or adjust the intensity of the plug-in lighting load in response to the received digital messages. An appliance, such as a television 144, may be plugged into one of the plug-in load control devices 140, and the plug-in load control device may be configured to turn the appliance on and off in response to the digital messages received via the RF signals 108.

Alternatively or in addition, the load control system 100 may comprise controllable receptacles for controlling plug-in electrical loads plugged into the receptacles. The load control system 100 may comprise one or more load control devices or appliances that are able to directly receive the wireless signals 108 from the system controller 110, such as a speaker 146 (e.g., part of an audio/visual or intercom system), which is able to generate audible sounds, such as alarms, music, intercom functionality, etc.

The load control system 100 may comprise one or more daylight control devices, e.g., motorized window treatments 150, such as motorized cellular shades, for controlling the amount of daylight entering the building in which the load control system is installed. The motorized window treatments 150 may be configured to receive digital messages via the RF signals 108 (e.g., from the system controller 110) and may be configured to adjust the position of a window treatment fabric in response to the received digital messages. The load control system 100 may comprise other types of daylight control devices, such as, for example, a cellular shade, a drapery, a Roman shade, a Venetian blind, a Persian blind, a pleated blind, a tensioned roller shade systems, an electrochromic or smart window, and/or other suitable daylight control device.

The load control system 100 may comprise one or more temperature control devices 160 (e.g., thermostats) for controlling a room temperature in each of the rooms 102, 104, 106. A temperature control device 160 may be coupled to a heating, ventilation, and air conditioning (HVAC) system 162 via a control link (e.g., an analog control link or a wired digital communication link). The temperature control device 160 may be configured to wirelessly communicate digital messages with a controller of the HVAC system 162. The temperature control device 160 may comprise a temperature sensor for measuring the room temperature of the respective room 102, 104, 106 and may control the HVAC system 162 to adjust the temperature in the room to a respective setpoint temperature.

The load control system 100 may comprise one or more other types of load control devices, such as, for example, a screw-in luminaire including a dimmer circuit and an incandescent or halogen lamp; a screw-in luminaire including a ballast and a compact fluorescent lamp; a screw-in luminaire including an LED driver and an LED light source; an electronic switch, controllable circuit breaker, or other switching device for turning an appliance on and off; a plug-in load control device, controllable electrical receptacle, or controllable power strip for controlling one or more plug-in loads; a motor control unit for controlling a motor load, such as a ceiling fan or an exhaust fan; a drive unit for controlling a motorized window treatment or a projection screen; motorized interior or exterior shutters; a thermostat for a heating and/or cooling system; a temperature control device for controlling a setpoint temperature of an HVAC system; an air conditioner; a compressor; an electric baseboard heater controller; a controllable damper; a variable air volume controller; a fresh air intake controller; a ventilation controller; hydraulic valves for use in radiators and a radiant heating system; a humidity control unit; a humidifier; a dehumidifier; a water heater; a boiler controller; a pool pump; a refrigerator; a freezer; a television or computer monitor; a video camera; an audio system or amplifier; an elevator; a power supply; a generator; an electric charger, such as an electric vehicle charger; and an alternative energy controller.

The load control system 100 may comprise one or more input devices, e.g., such as battery-powered remote control devices 170, occupancy sensors 172, and/or daylight sensors 174. The input devices may be fixed or movable input devices. The battery-powered remote control devices 170, the occupancy sensors 172, and/or the daylight sensors 174 may be wireless control devices (e.g., RF transmitters) configured to transmit digital messages via the RF signals 108 to the system controller 110 (e.g., directly to the system controller). For example, the battery-powered remote control device 170 may be configured to transmit digital messages to the system controller 110 via the RF signals 108 in response to an actuation of one or more buttons of the battery-powered remote control device. The system controller 110 may be configured to transmit one or more digital messages to the load control devices (e.g., the dimmer switches 120, the LED drivers 130, the plug-in load control devices 140, the motorized window treatments 150, and/or the temperature control devices 160) in response to the digital messages received from the battery-powered remote control devices 170, the occupancy sensors 172, and/or the daylight sensors 174. The battery-powered remote control devices 170, the occupancy sensors 172, and/or the daylight sensors 174 may be configured to transmit digital messages directly to the dimmer switches 120, the LED drivers 130, the plug-in load control devices 140, the motorized window treatments 150, and the temperature control devices 160. The input devices may also comprise a door entrance sensor, a door movement sensor, or a keycard door opening device.

The occupancy sensors 172 may be configured to detect occupancy and vacancy conditions in the rooms 102, 106 in which the occupancy sensors are mounted. The occupancy sensors 172 may transmit digital messages to the system controller 110 via the RF signals 108 in response to detecting the occupancy or vacancy conditions. The system controller 110 may be configured to turn one or more of the lighting loads 122 and the LED light sources 132 on and off in response to receiving an occupied command and a vacant command, respectively. The occupancy sensors 172 may operate as vacancy sensors, such that the lighting loads are merely turned off in response to detecting a vacancy condition (e.g., and not turned on in response to detecting an occupancy condition). Examples of RF load control systems having occupancy and vacancy sensors are described in greater detail in commonly-assigned U.S. Pat. No. 8,009,042, issued Aug. 30, 2011, entitled RADIO-FREQUENCY LIGHTING CONTROL SYSTEM WITH OCCUPANCY SENSING; U.S. Pat. No. 8,199,010, issued Jun. 12, 2012, entitled METHOD AND APPARATUS FOR CONFIGURING A WIRELESS SENSOR; and U.S. Pat. No. 8,228,184, issued Jul. 24, 2012, entitled BATTERY-POWERED OCCUPANCY SENSOR, the entire disclosures of which are hereby incorporated by reference.

The daylight sensors 174 may be configured to measure a total light intensity in the room 102, 104 in which the daylight sensor is installed. The daylight sensors 174 may transmit digital messages including the measured light intensity to the system controller 110 via the RF signals 108 for controlling the intensities of one or more of the lighting loads 122 and the LED light sources 132 in response to the measured light intensity. Examples of RF load control systems having daylight sensors are described in greater detail in commonly-assigned U.S. Pat. No. 8,410,706, issued Apr. 2, 2013, entitled METHOD OF CALIBRATING A DAYLIGHT SENSOR; and U.S. Pat. No. 8,451,116, issued May 28, 2013, entitled WIRELESS BATTERY-POWERED DAYLIGHT SENSOR, the entire disclosures of which are hereby incorporated by reference.

The load control system 100 may comprise one or more wireless temperature sensors 190 located in the rooms 102, 104, 106 for measuring the room temperatures. The temperature sensors 190 may communicate via wired and/or wireless communications with the system controller 110 and/or the temperature control devices 160. Though the temperature sensors 190 are external to the temperature control devices 160, the temperature sensors 190 may be incorporated in the temperature control devices 160. The HVAC system 162 may be controlled by the temperature control devices 160 (e.g., in response to sensor information from the temperature sensors 190, instructions from the system controller 110, actuation of one or more buttons by a user, etc.). The HVAC system 162 may turn a compressor on and off for cooling the rooms 102, 104, 106 and to turn a heating source on and off for heating the rooms in response to the control signals received from the temperature control devices 160. The HVAC system 162 may turn a fan of the HVAC system on and off in response to the control signals received from the temperature control devices 160. The temperature control devices 160 and/or the HVAC system 162 may be configured to control one or more controllable dampers to control the air flow in each of the rooms 102, 104, 106.

The load control system 100 may comprise other types of input devices, such as, for example, temperature sensors, humidity sensors, radiometers, cloudy-day sensors, shadow sensors, pressure sensors, smoke detectors, carbon monoxide detectors, air-quality sensors, motion sensors, security sensors, proximity sensors, fixture sensors, partition sensors, keypads, multi-zone control units, slider control units, kinetic or solar-powered remote controls, key fobs, cell phones, smart phones, tablets, personal digital assistants, personal computers, laptops, timeclocks, audio-visual controls, safety devices, power monitoring devices (e.g., such as power meters, energy meters, utility submeters, utility rate meters, etc.), central control transmitters, residential controllers, commercial controllers, industrial controllers, and/or any combination thereof.

The system controller 110 may be configured to be coupled to a network, such as a wireless or wired local area network (LAN), e.g., for access to the Internet. The system controller 110 may be wirelessly connected to the network, e.g., using Wi-Fi technology. The system controller 110 may be coupled to the network via a network communication bus (e.g., an Ethernet communication link).

The system controller 110 may be configured to communicate via the network with one or more mobile devices 182, such as, a personal computing device and/or a wearable wireless device. The mobile device 182 may be located on an occupant 180, for example, may be attached to the occupant's body or clothing or may be held by the occupant. The mobile device 182 may be characterized by a unique identifier (e.g., a serial number or address stored in memory) that uniquely identifies the mobile device 182 and thus the occupant 180. Examples of personal computing devices may include a smart phone (e.g., an iPhone® smart phone, an Android® smart phone, or a Blackberry® smart phone), a laptop, and/or a tablet device (e.g., an iPad® hand-held computing device). Examples of wearable wireless devices may include an activity tracking device (e.g., such as a FitBit® device, a Misfit® device, and/or a Sony Smartband® device), a smart watch, smart clothing (e.g., OMsignal® smartwear, etc.), and/or smart glasses (e.g., such as Google Glass® eyewear).

The mobile device 182 may be configured to transmit digital messages to the system controller 110, for example, in one or more Internet Protocol packets. For example, the mobile device 182 may be configured to transmit digital messages to the system controller 110 over the LAN and/or via the Internet. The mobile device 182 may be configured to transmit digital messages over the Internet to an external service (e.g., If This Then That (IFTTT®) service), and then the digital messages may be received by the system controller 110. The mobile device 182 may transmit the RF signals 108 via a Wi-Fi communication link, a Wi-MAX communications link, a Bluetooth® communications link, a near field communication (NFC) link, a cellular communications link, a television white space (TVWS) communication link, or any combination thereof. Alternatively or additionally, the mobile device 182 may be configured to transmit RF signals according to the proprietary protocol.

The load control system 100 may comprise other types of network devices coupled to the network, such as a desktop personal computer, a Wi-Fi or wireless-communication-capable television, or any other suitable Internet-Protocol-enabled device. Examples of load control systems operable to communicate with mobile and/or network devices on a network are described in greater detail in commonly-assigned U.S. Patent Application Publication No. 2013/0030589, published Jan. 31, 2013, entitled LOAD CONTROL DEVICE HAVING INTERNET CONNECTIVITY, the entire disclosure of which is hereby incorporated by reference.

The operation of the load control system 100 may be programmed and configured using, for example, the mobile device 182 or other network device (e.g., when the mobile device is a personal computing device) during a configuration (or commissioning) procedure. The mobile device 182 may execute a graphical user interface (GUI) configuration software for allowing a user to program how the load control system 100 will operate. For example, the configuration software may run as a PC application or a web interface. The configuration software and/or the system controller 110 (e.g., via instructions from the configuration software) may generate a load control database that defines the operation of the load control system 100. For example, the load control database may include information regarding the operational settings of different load control devices of the load control system (e.g., the dimmer switch 120, the LED drivers 130, the plug-in load control devices 140, the motorized window treatments 150, and/or the temperature control devices 160). The load control database may comprise information regarding associations between the load control devices and the input devices (e.g., the battery-powered remote control devices 170, the occupancy sensors 172, and/or the daylight sensors 174). The load control database may comprise information regarding how the load control devices respond to inputs received from the input devices. Examples of configuration procedures for load control systems are described in greater detail in commonly-assigned U.S. Pat. No. 7,391,297, issued Jun. 24, 2008, entitled HANDHELD PROGRAMMER FOR A LIGHTING CONTROL SYSTEM; U.S. Patent Application Publication No. 2008/0092075, published Apr. 17, 2008, entitled METHOD OF BUILDING A DATABASE OF A LIGHTING CONTROL SYSTEM; and U.S. Patent Application Publication No. 2014/0265568, published Sep. 18, 2014, entitled COMMISSIONING LOAD CONTROL SYSTEMS, the entire disclosures of which are hereby incorporated by reference.

The mobile device 182 may comprise one or more sensing devices for sensing one or more parameters (e.g., biometric data) that define the physical condition (e.g., behavior, movement, comfort, and/or health) of the occupant 180. For example, the sensing devices of the mobile device 182 may include an accelerometer for monitoring the movement of the occupant. The mobile device 182 may comprise sensing devices for monitoring the heart rate, the blood pressure, the body temperature, the blood sugar, and/or the perspiration level of the occupant 180. The mobile device 182 may include any combination of sensing devices. The mobile device 182 may be configured to transmit digital messages to the system controller 110 including data regarding the parameters measured by the sensing devices of the mobile device 182.

The system controller 110 may be configured to deduce the state or physical condition of the occupant 180 using the parameters measured by the sensing devices of the mobile device 182. For example, the system controller 110 may be configured to determine that the occupant 180 is sleeping or that the stress level of the occupant 180 is increasing in response to one or more of the parameters measured by the sensing devices of the mobile device 182.

The system controller 110 may be configured to determine the location of the mobile device 182 and/or the occupant 180. The system controller 110 may be configured to control (e.g., automatically control) the load control devices (e.g., the dimmer switches 120, the LED drivers 130, the plug-in load control devices 140, the motorized window treatments 150, and/or the temperature control devices 160) in response to determining the location of the mobile device 182 and/or the occupant 180. The system controller 110 may be configured to control the load control devices according to occupant control parameters associated with the occupant 180. The occupant control parameters may be predetermined or preset settings for the occupant 180, biometric data for the occupant 180, and/or user input data received from the occupant 180 via the mobile device 182.

The system controller 110 may be configured to determine the location of the mobile device 182 using triangulation. Since the load control devices of the load control system 100 may be mounted in fixed locations, the load control devices may measure the signal strength of RF signals received from the mobile device 182. The load control devices may transmit these signals strengths to the system controller 110, which may be configured to determine the location of the mobile device 182 using the signal strengths. One or more load control devices of the load control system 100 may be movable devices. As such, the load control system 100 may comprise fixed and movable load control devices.

The mobile device 182 may be configured to determine its location and to transmit the location information to the system controller 110 and/or the load control devices. For example, the mobile device may be configured to determine its location based on the signal strengths of RF signals received directly from three or more of the load control devices. The mobile device 182 may be configured to determine its location based on global positioning system (GPS) information from a GPS receiver (e.g., a geolocation).

The load control system 100 may comprise one or more beacon devices 184 for transmitting the beacon signals. A load control device (e.g., a fixed-location control device) of the load control system 100 may be configured to transmit the beacon signals. The mobile device may be configured to determine its location in response to a beacon signal (e.g., transmitted using a short-range and/or low-power RF technology, such as Bluetooth technology) received when located near a control device that is presently transmitting the beacon signal.

A beacon signal may comprise a unique identifier identifying the location of the load control device that transmitted the beacon signal. Since the beacon signal may be transmitted using a short-range and/or low-power technology, the unique identifier may indicate the approximate location of the mobile device 182. The mobile device 182 may be configured to use the unique identifier to retrieve the location of the mobile device via the Internet. The mobile device 182 may be configured to transmit the location (e.g., unique identifier or other indication of location) to the system controller 110, which may be configured to automatically control the load control devices in response to the location of the mobile device. The mobile device 182 may be configured to transmit the unique identifier to the system controller 110, which may be configured to determine the location of the mobile device 182 using the unique identifier (e.g., using data stored in memory or retrieved via the Internet). The system controller 110 may be configured to transmit the location back to the mobile device 182 and/or automatically control the load control devices in response to the location of the mobile device 182.

The system controller 110 may be configured to control (e.g., automatically control) the load control devices in response to determining the location of the mobile device 182, for example, when one of the occupancy sensors 172 indicates that the space (e.g., room), which was indicated as the location of the mobile device, is occupied. The mobile device 182 may be configured to directly receive a digital message indicating the occupancy condition from one of the occupancy sensors 172, to determine that the occupancy sensor is located in the room in which the mobile device is located, and/or to transmit a command to control the load control devices in the response to receiving the digital message indicating the occupancy condition (e.g., transmitted to the system controller 110 or directly to the load control devices).

An input device (e.g., the battery-powered remote control devices 170, the occupancy sensors 172, and/or the daylight sensors 174) may be configured to determine its location. The input device may be configured to determine its location in response to determining a signal strength signature at the present location. The signal strength signature may be a pattern of signal strength measurements to and from the fixed-location control devices (e.g., the load control devices) of the load control system 100. The input device may be configured to use a neural network to learn a signal strength signature in each of the rooms 102, 104, 106. For example, the input device may learn the signal strength signature using signal strengths measured when the input device is in one of the rooms 102, 104, 106 during a configuration or setup procedure of the load control system 100 to determine the weights of the neural network that will allow the input device to recognize these patterns. The input device may alter its operation in response to the determined location and/or transmit the determined location to the load control devices and/or system controller 110. The input devices and/or the system controller 110 may be configured to determine the locations of the input devices using any of the procedures described herein.

The load control system 100 may comprise one or more camera devices 176 for recording video surveillance of the rooms 102, 104, 106. A camera device 176 may be configured to transmit video recordings to the system controller 110. The system controller 110 may be configured to determine the presence of the occupant 180 in the room 104 by processing the images received from the camera devices 176. For example, the system controller 110 may identify movement in the room 104, that a person is in the room 104, a number of people in the room 104, and/or a specific person in the room 104 from the images received from the camera device 176. The system controller 110 may identify a specific person in the room using facial recognition technology, for example.

An image of the face of the occupant 180 or predetermined measurements on the occupant 180 may be stored for being compared with the images received from the camera device 176. Other points of reference on the body of the occupant 180 may similarly be stored (e.g., locally or remotely) to identify the occupant 180 from the images received from the camera device 176. The occupant 180 may be of different occupant types. For example, the occupant 180 may be a human, the occupant 180 may also, or alternatively, be a type of animal (e.g., a pet) or a plant. The occupant type may refer to an adult human or a child human. The system controller 110 may be programmed to identify different occupants 180 by taking images and storing the distance between points of reference in images that identify the occupant 180 that can be compared against later images for identifying the occupant 180. This may allow the system controller 110 to differentiate between different occupants and/or occupant types. The system controller 110 may also be preconfigured to distinguish between the different occupants and/or occupant types based on size in an image.

The load control system 100 may comprise one or more microphones 192 for recording audio in the rooms 102, 104, 106. A microphone 192 may be configured to transmit audio recordings to the system controller 110. The system controller 110 may be configured to determine the presence of the occupant 180 in the room 104 by processing the audio received from the microphone 192. For example, the system controller 110 may identify movement in the room 104, that a person is in the room 104, a number of people in the room 104, and/or a specific person in the room 104 from the audio received from the microphone 192. The volume of the audio received may indicate the relative distance of the occupant 180 from the microphone 192 and/or the number of people in the room.

The load control system 100 may comprise one or more fingerprint scanners 194 for detecting the fingerprint of the occupant 180 in the rooms 102, 104, 106. The identification of the fingerprint of the occupant 180 in the room 104 may indicate the location of the occupant 180. The mobile device 182 may also, or alternatively, be used to scan the fingerprint of the occupant 180. The fingerprint scanner 194 may be configured to transmit fingerprint data to the system controller 110. The system controller 110 may be configured to determine the presence of the occupant 180 in the room 104 by processing the fingerprint data to identify the fingerprint of the occupant 180.

The system controller 110 may set the lighting control device and/or other control-target devices to a preset of the occupant 180 based on the detection of the occupant 180 within the space of the control-target device. The system controller 110 may set the control-target devices to different presets based on the type of occupant 180 (e.g., adult human, child human, other types of animals, plants) and/or different specific occupants.

A sensor (e.g., an occupancy sensor) may be configured to control the status of a control-target device (e.g., turn lights on/off, raise/lower shades, etc.) and the system controller 110 may be configured to determine and set the preset level of the control-target device based on the detection of a mobile device 182 (e.g., wearable wireless device) within the space of the control-target device. For example, an occupancy sensor may turn the lighting of a space on/off based on the detection of an occupant, while the system controller 110 may set the lighting control device or other control-target device to a preset of the occupant 180 based on the detection of the occupant's mobile device 182 within the space of the control-target device.

The system controller 110 may be configured to control (e.g., automatically control) the load control devices in response to determining the location of the mobile device 182 and/or the occupant 180. For example, the system controller 110 may be configured to control (e.g., automatically control) the load control devices according to predetermined or preset settings for the occupant 180. A preset setting may identify preset lighting intensities of the lighting loads, preset positions of the motorized window treatments 150, and/or preset setpoint temperatures of the temperature control devices 160. The system controller 110 may control the load control devices in the rooms according to the occupant's preset settings as the occupant moves around the building (e.g., to "follow" the occupant around the building). The preset settings may be "universal" settings (e.g., the preset settings may be the same for each room of the building), or may be room settings (e.g., the preset settings may be different for each room). The preset settings may be determined based on the time of day and/or year. For example, the lighting loads 122 and LED light sources 132 may automatically be illuminated dimly when controlled (e.g., automatically controlled) at night in response to the location of the mobile device 182 and/or occupant 180. The level at which the load control devices and/or electrical loads are controlled may be dependent upon the distance from the mobile device 182 and the controlled load control device and/or electrical load. Since the mobile device 182 may uniquely identify the occupant 180, the preset settings may be different for different occupants of the rooms. Since the system controller 110 may uniquely identify different types of occupants 180, the preset settings may be different for different types of occupants of the rooms.

Figure 2:
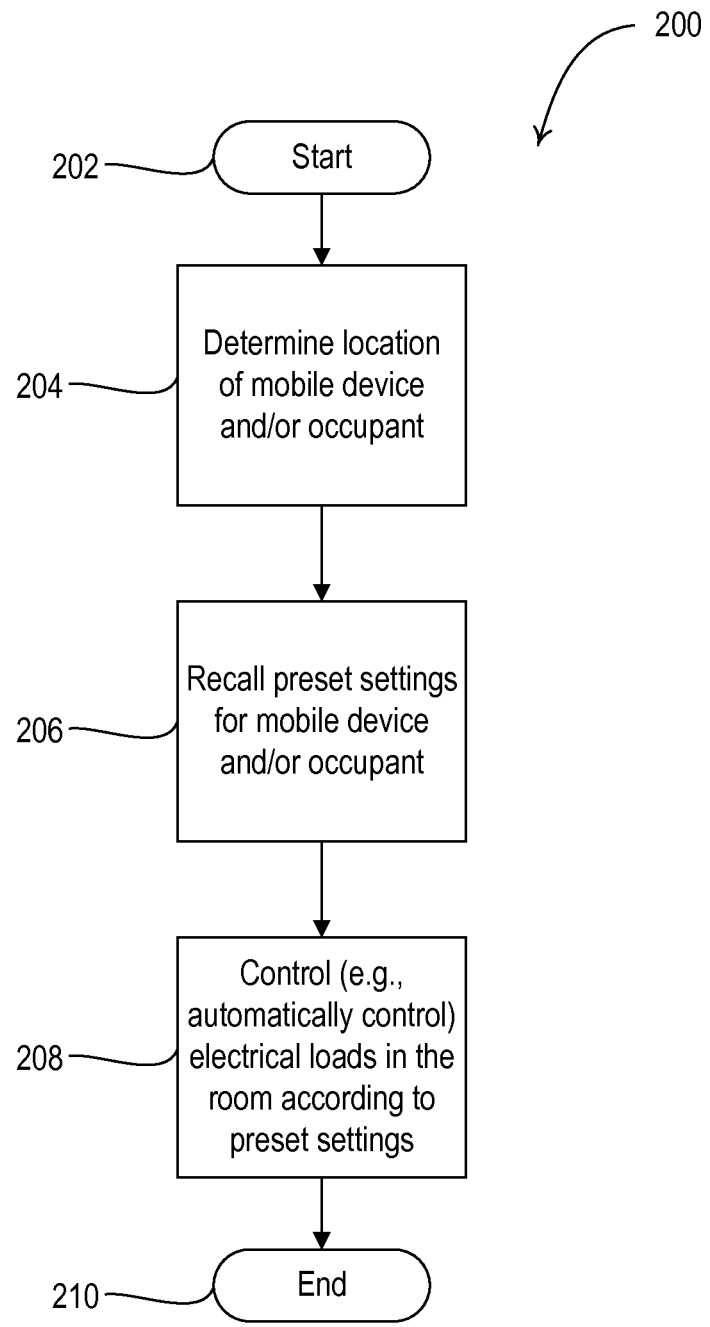
FIG. 2 is a flowchart of an example control procedure for automatically controlling electrical loads in response to the location of a mobile device and/or an occupant.

FIG. 2 is a simplified flowchart of an example control procedure 200 for controlling (e.g., automatically controlling) one or more electrical loads in response to the location of the mobile device 182 and/or the occupant 180. For example, the control procedure 200 may be executed by the system controller 110. At 202, the example control procedure 200 may start. At 204, the system controller 110 may determine a location of a mobile device 182 and/or occupant 180. For example, the system controller 110 may determine a location of a mobile device 182 and/or occupant 180 using one or a combination of triangulation, received signals from the mobile device 182, a sensor, a camera, beacon signals, a microphone, fingerprint detection, and/or the like.

At 206, the system controller 110 may recall (e.g., load) preset settings based on the mobile device 182 and/or occupant 180, for example, as described herein. At 208, the system controller 110 may control (e.g., automatically control) electrical loads in the space (e.g., room) according to the recalled preset settings of the mobile device 182 and/or occupant 180. For example, the system controller 110 may automatically control electrical loads in the room according to predetermined or preset settings for the occupant 180, which may be room specific settings. At 210, the example control procedure 200 may end.

Since there may be multiple occupants in a single room, the system controller 110 may be configured to control (e.g., automatically control) one or more of the load control devices using a predetermined priority (e.g., a tiered hierarchy) of occupants to determine which occupant's preset settings get priority. For example, the system controller 110 may automatically control the load control devices to a preset setting of the mobile device 182 and/or occupant 180 in the room that has the highest priority. The priorities and/or tiered hierarchy may be determined during a configuration procedure of the load control system 100 and may be stored in memory in the system controller 110. The priority may be based on the location of the occupants within the space. For example, the occupant closest to or furthest from a door or window (e.g., for control of the windows) may be assigned the highest priority, the occupant closest to the load control device may be assigned the highest priority, the occupant closest the load may be assigned the highest priority, etc. Occupant priority may be determined based on the amount of time in the space. For example, occupants that have been in the location longer may be given higher priority. The system controller 110 may give priority to an occupant 180 that has a meeting in the space or otherwise has primary occupancy over the space (e.g., an occupant's assigned cubical space or office space). The system controller 110 may have access to the occupant's calendar on the mobile device 182 or other computing device to determine whether the occupant 180 has a meeting in the space. The system controller 110 may have stored thereon or access to an association of occupant's to office spaces (e.g., occupant cubical spaces and/or offices).

Where different occupant types are in a room, the adult occupants may be given priority over child occupants. Human occupants may be given priority over other animal occupants and/or plant occupants. Other animal occupants may be given priority over plant occupants. Priority may also, or alternatively, be based on a history of past actions by an occupant. For example, if the occupant 180 selects a preference more than a predetermined number of times (e.g., more than once) within a predefined time period (e.g., last half hour, hour, day etc.), the selections performed more than the predetermined number of times may be given a lesser priority or no priority.

Figure 3:
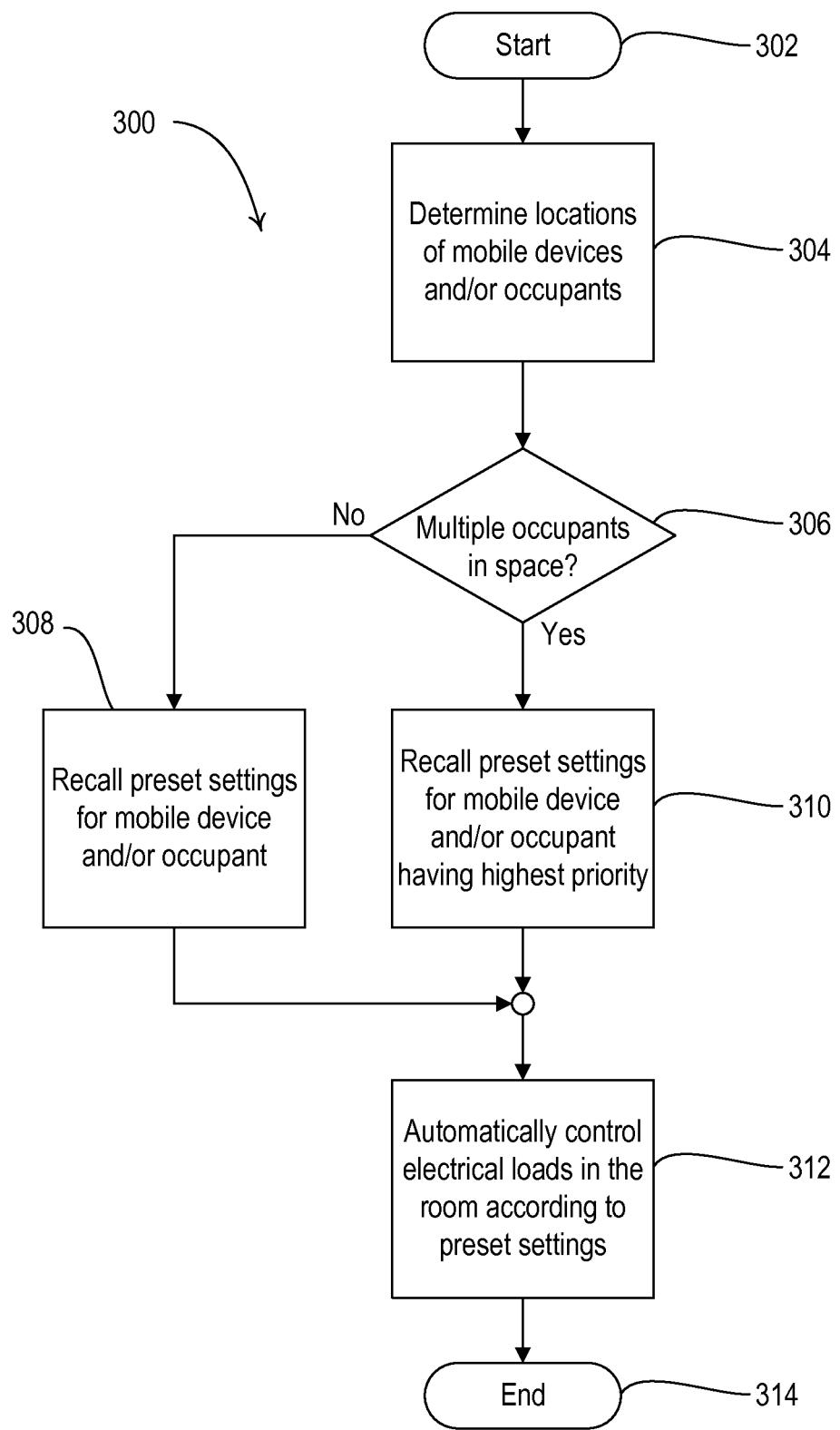
FIG. 3 is a flowchart of an example control procedure for automatically controlling electrical loads in response to the location of one or more mobile devices and/or occupants when there may be multiple mobile devices and/or occupants in a single space.

FIG. 3 is a flowchart of an example control procedure 300 for controlling (e.g., automatically controlling) one or more electrical loads in response to the location of one or more mobiles devices and/or occupants when there may be multiple mobile devices and/or occupants in a single space. For example, the control procedure 300 may be executed by the system controller 110. At 302, the example control procedure 300 may start. At 304, the system controller 110 may determine the location of one or more mobile devices 182 and/or occupants 180, for example, as described herein. At 306, the system controller 110 may determine if multiple occupants are in the space. The system controller 110 may determine occupancies based on the presence of an occupant's mobile device 182 (e.g., wearable wireless device), a sensor, a camera, etc. If the system controller 110 determines that there is one occupant 180 in the space, then at 308 the system controller 110 may recall preset settings for the mobile device 182 and/or the occupant 180 accordingly, for example, as described herein.

If the system controller 110 determines that there are multiple occupants 180 in the space at 306, then at 310 the system controller 110 may recall preset settings for the mobile device 182 and/or the occupant 180 having the highest priority, for example, as described herein. At 312, the system controller 110 may control (e.g., automatically control) one or more control-target devices (e.g., electrical loads) according to the preset settings of the occupant 180 having the highest priority. At 314, the example control procedure 300 may end.

The system controller 110 may be configured to control (e.g., automatically control) the load control devices according to the occupant's preset settings in response to determining the location of the mobile device 182 in combination with information from one or more other control-source devices. For example, the system controller 110 may be configured to automatically control the load control devices according to the occupant's preset settings in response to determining the location of the mobile device 182 as well as determining that one of the occupancy sensors 172 has determined that the room in which the mobile device 182 is located is occupied.

Figure 4:
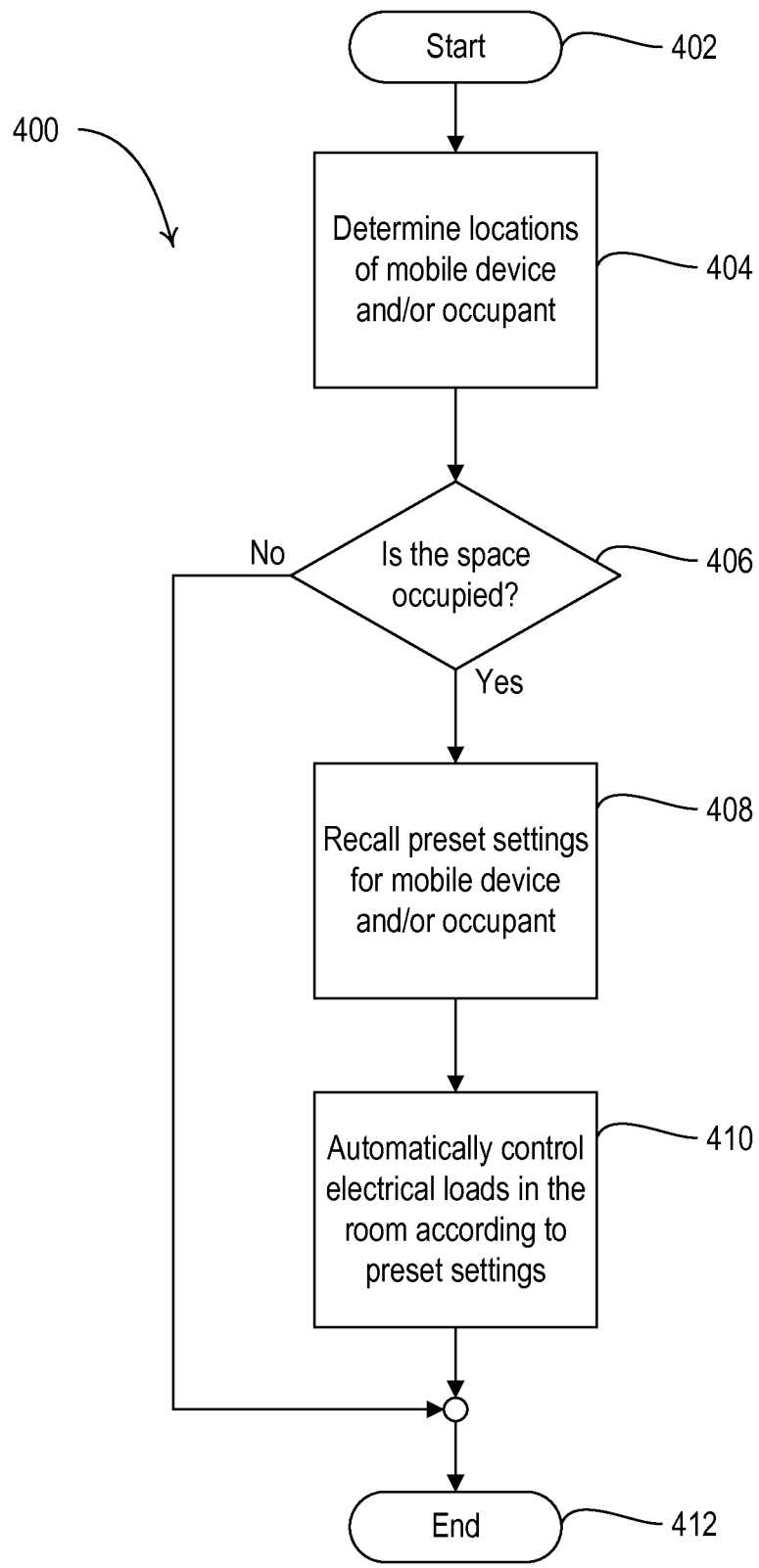
FIG. 4 is a flowchart of an example control procedure for automatically controlling electrical loads in response to the location of a mobile device and/or an occupant if the space in which the mobile device and/or occupant is located is occupied.

FIG. 4 is a flowchart of an example control procedure 400 for controlling (e.g., automatically controlling) one or more electrical loads in response to the location of the mobile device 182 and/or the occupant 180. For example, the control procedure 400 may be executed by the system controller 110. The example control procedure 400 may start at 402. At 404, the system controller 110 may determine the location of one or more mobile devices 182 and/or occupants 180. At 406, the system controller 110 may determine whether the space is occupied, for example, using information from the one or more mobile devices 182, sensor information, a camera, beacon signals, a microphone, fingerprint detection, etc. If the system controller 110 determines that the space is not occupied at 406, then the example control procedure 400 may end at 412.

If the system controller 110 determines that the space is occupied at 406, then at 408 the system controller 110 may recall preset settings for a mobile device 182 and/or occupant 180 located in the space, and control (e.g., automatically control) one or more control-target devices (e.g., electrical loads) according to the preset settings at 410. As such, the system controller 110 may be configured to control one or more electrical loads in response to the location of the mobile device 182 and/or the occupant 180 if the space in which the mobile device and/or occupant is located is occupied. The system controller 110 may be configured to control the load control devices and/or electrical loads in a room to save energy when the mobile device 182 and/or the occupant 180 is not located in the room (e.g., by turning off or reducing the amount of power delivered to the load control devices and/or electrical loads).

The system controller 110 may be configured to control (e.g., automatically control) the load control devices according to the occupant's preset settings in response to determining the location of the mobile device 182 when the occupant 180 actuates a button on one of the load control devices (e.g., one of the dimmer switches 120) in the room in which the mobile device 182 is located. For example, the dimmer switch on which the button was actuated may be configured to determine the unique identifier of the mobile device 182 (e.g., the closest mobile device 182 if more than one mobile device 182 is determined to be present in the room) and to control the controlled lighting load in response to the occupant's preset settings (e.g., which may be stored in memory in the dimmer switch and/or the system controller 110, which may communicate the settings to the dimmer switch).

The system controller 110 may be configured to learn the preset settings for each occupant of the building. For example, each time that an occupant 180 turns on a specific lighting load by actuating a button of the corresponding dimmer switch 120, the system controller 110 may be configured to store a desired intensity level to which the intensity of the lighting load was controlled as well as the identity of the occupant 180. The identity of the occupant may be the unique identifier of the mobile device 182 that is presently located in the room of that specific dimmer switch (e.g., or the mobile device 182 closest to the dimmer switch if more than one mobile device 182 is determined to be present in the room). If the occupant repetitively controls the lighting load to the same desired intensity level upon entering the room, the system controller 110 may be configured to store the desired intensity level as the preset level in the room for that occupant. When the actuator of that specific dimmer switch is subsequently actuated and the occupant 180 and/or occupant's mobile device 182 is located in the room of the dimmer switch, the system controller 110 may be configured to cause the dimmer switch to control the intensity of the lighting load to the desired intensity level (e.g., the preset level) that is stored in memory. The system controller 110 may be configured to cause (e.g., automatically cause) the dimmer switch to control the intensity of the lighting load to the desired intensity level when the occupant and/or the occupant's mobile device 182 enters the room of the dimmer switch (e.g., without required actuation of the button of the dimmer switch).

The system controller 110 may be configured to control (e.g., predictively control) one or more load control devices and/or electrical loads in response to detecting movement of an occupant. The system controller 110 may be configured to determine the direction in which the occupant 180 is moving (e.g., a trajectory of the occupant) in response to sensor information, analyzing the direction of movement in images from a camera, and/or detecting the direction that the mobile device 182 is moving through the building. For example, the system controller 110 may be configured to control the load control devices and/or the electrical loads at the intended destination of the occupant to the occupant's preset settings before the occupant arrives at the destination. The system controller 110 may be configured to learn the intended destination of the occupant by monitoring the occupant's movements over a number of days. For example, the occupant 180 may get up in the middle of each night and walk to the kitchen for a glass of water. The system controller 110 may be configured to detect the occupant's movements and the time of day, and determine to predictively turn the lights on the kitchen and/or along the pathway to the kitchen. The system controller 110 may determine to predictively control a control-target device at defined time period when the system controller 110 detects the occupant's movements in a location or toward a location occurred within a defined time period more than a predefined number of times (e.g., consecutive times) over a certain period (e.g., number of hours, number of days, number of weeks, etc.). The predictive control of the control target device may be set based on the user's control of the control-target device. For example, the user's control of the control-target device may be recorded and set as a preset at the system controller 110 for automatically controlling the control-target at the defined period of time. The user may enable/disable the predictive control functionality of the system controller 110 for different control target devices or altogether. The user may also, or alternatively, enable/disable the predictive control functionality of the system controller 110 for certain times of day or times of the week (e.g., weekends, etc.).

When the occupant 180 is entering or exiting the building, the system controller 110 may be configured to control the load control devices and/or electrical loads differently depending upon the origin and/or destination of the occupant 180. For example, the system controller 110 may be configured to determine that the occupant 180 is going on vacation by accessing the occupant's calendar on the mobile device 182 and automatically select a vacation mode when the occupant 180 leaves the building. The occupant 180 may be prompted by the mobile device 182 to allow the system controller 110 to access to the calendar on the mobile device 182. The system controller 110 may be configured to determine that the occupant 180 is headed home, for example, using global positioning system (GPS) data (e.g., geolocation) from the mobile device 182 and/or the present time of day, and automatically control the load control devices and/or electrical loads according to a preset (e.g., a "welcome home" preset). The system controller 110 may be configured to lock or unlock a controllable lock on the building in response to determining that the occupant 180 is approaching the building or has just left the building, respectively. The system controller 110 may be configured to arm or disarm a security system of the building in response to determining that the occupant 180 is approaching the building or has just left the building, respectively.

The mobile device 182 and/or the input devices (e.g., such as the battery-powered remote control devices 170) may be configured to operate differently depending upon the present location of the mobile device 182. When a control application is started on the mobile device 182 (e.g., and the mobile device has a visual display), the mobile device 182 may be configured to display a screen for controlling a respective location when the mobile device 182 is at or near (e.g., within a predefined distance of) the location. For example, the mobile device 182 and/or an input device (e.g., remote control device 170 located in the living room) may be configured to display a "living room" home screen when the mobile device is presently located in the living room.

The mobile device 182 may be configured to re-order lists or formats of electrical loads, load control devices, input devices, control buttons, and/or presets displayed on the visual display in response to the location of the mobile device 182. The mobile device 182 may display the items in a list in a different order or in a different location on the display in response to detecting different locations of the mobile device 182. For example, the mobile device 182 may determine the more commonly selected items by one or more users for a respective location and may display the more commonly selected items in a more convenient location on the display (e.g., higher in a displayed list, closer to the top of the displayed list, or closer to a side of the display for easier access for selection by the user) when the mobile device is at or near (e.g., within a predefined distance of) the location. The mobile device 182 may store the number of times different items are selected and may re-configure the display configuration for the items when an item is selected more than another item (e.g., more than a predefined number of times to prevent reconfiguration each time an item is selected more than another). The mobile device 182 may be configured to display messages and/or warnings to the occupant 180 depending upon the present location, for example, to inform the occupant of burnt-out lamps or faulty control devices in the present room. The mobile device 182 may be able to display a warning when the time-of-day pricing for electricity has exceeded a predetermined threshold. The warning may be received by the system controller 110 (e.g., from an electricity provider) and may be sent in a digital message to the mobile device 182 or may be sent as a warning directly to the mobile device 182.

The mobile device 182 may use the location of the device to determine the display configuration and/or warnings for being displayed at or near the location. The mobile device 182 may determine the location locally (e.g., via geolocation, triangulation, beacons, etc.) or as an indication from the system controller 110. The system controller 110 may also, or alternatively, determine the location of the mobile device and may provide the display, lists, and/or warnings to the mobile device 182 for display on the mobile device.

Figures 5, 6:
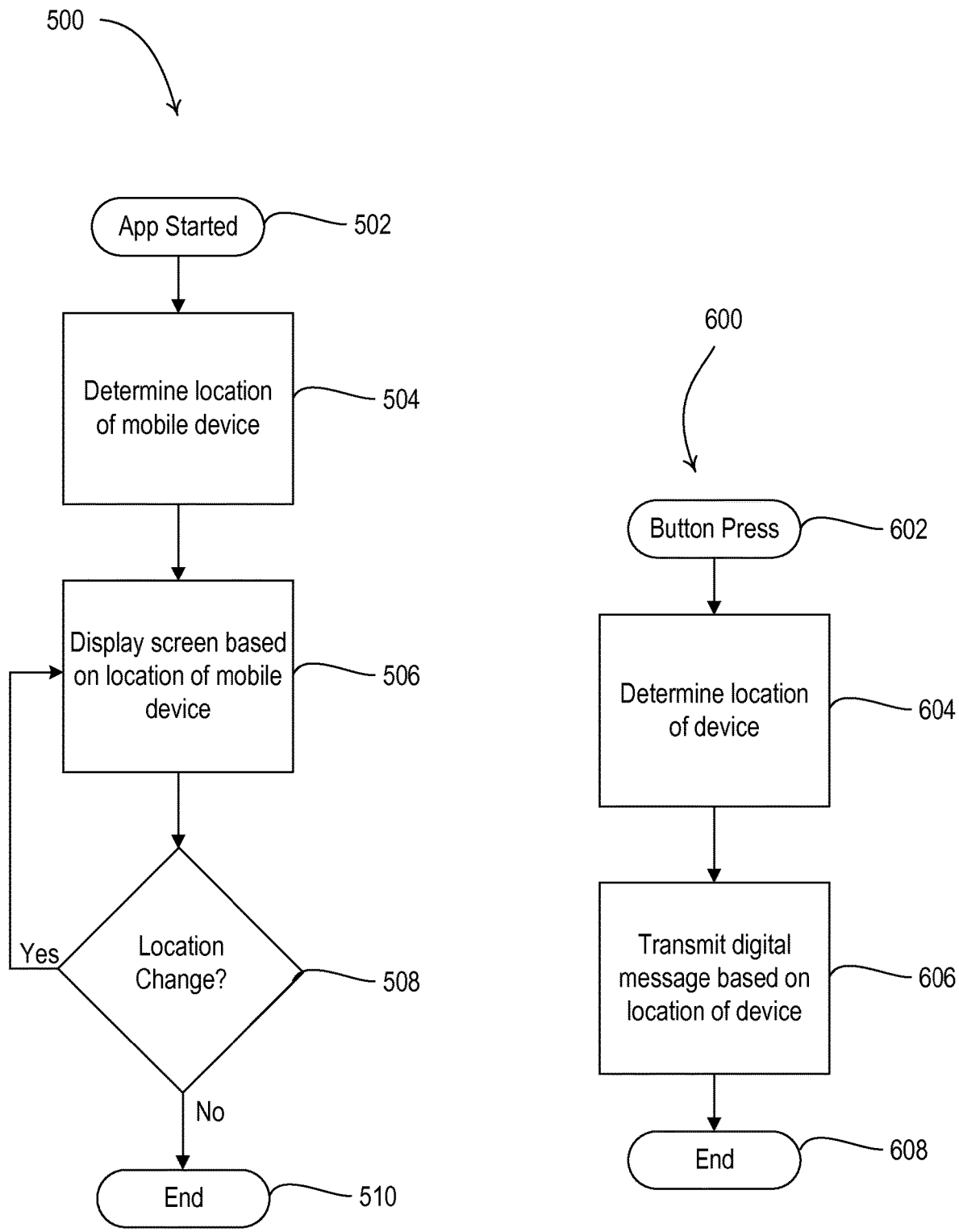
FIG. 5 is a flowchart of an example application startup procedure that may be executed by a mobile device.
FIG. 6 is a flowchart of an example button press procedure that may be executed by a remote control device and/or a mobile device.

FIG. 5 is a flowchart of an example application procedure 500 that may be executed by the mobile device 182. Portions of the procedure 500 may be performed by the system controller 110. At 502, an application on the mobile device 182 may be started. At 504, the mobile device 182 and/or the system controller 110 may determine the location of the mobile device 182, for example, as described herein. At 506, the mobile device 182 may display a screen (e.g., home screen) based on the location of the mobile device 182, for example, as described herein. For example, the mobile device 182 may display a re-ordered list or format of electrical loads, load control devices, input devices, control buttons, and/or presets, display messages to the occupant 180, and/or the like on its display in response to the location of the mobile device 182. The information and/or display configuration may be determined locally at the mobile device 182 and/or at the system controller 110. At 508, the mobile device 182 and/or the system controller 110 may determine whether the location of the mobile device 182 has changed. If the location of the mobile device has changed, the method may return to 506 to determine the screen (e.g., screen configuration) to display based on the location of the mobile device 182. At 510, the example procedure 500 may end.

The battery-powered remote control devices 170 may be configured to transmit different digital messages in response to the actuation of a single button or buttons depending upon the location of the remote control device 170. For example, actuation of a preset button of one of the remote control devices 170 may select a first preset for controlling one or more control-target devices when the remote control device 170 is located in a first room and may select a second preset for controlling one or more control-target devices when the remote control device 170 is located in a second room. The control-target devices in the first room may be different devices than the control-target devices in the second room. The presets for each location may be stored at the remote-control device 170, or the remote-control device may transmit the same digital message and a location of the device, which may be interpreted differently at the system controller 110 and/or the control-target devices based on the location. The location of the remote control device 170 may be determined at the remote control device 170 via a digital message from the system controller 110 or a digital message from the mobile device 182. The location of the remote control device 170 may also, or alternatively, be determined at the remote control device 170 similar to how the mobile device 182 may determine its location, for example.

FIG. 6 is a flowchart of an example button press procedure 600 that may be executed by the remote control devices 170, the mobile device 182, and/or the system controller 110. At 602, a button on a remote control device 170 or a mobile device 182 may be actuated. At 604, the remote control device 170, the mobile device 182, and/or the system controller 110 may determine the location of the remote control device 170 or the mobile device 182. At 606, the remote control device 170, the mobile device 182, and/or the system controller 110 may transmit a digital message based on the location of the remote control device 170 or the mobile device 182. For example, the remote control device 170 or the mobile device 182 may transmit different digital messages (e.g., for controlling different devices and/or different instructions for control) in response to the actuation of a single button depending upon its location. The remote control device 170 or the mobile device 182 may transmit different digital messages that indicate the devices location and the system controller 110 may transmit different load control messages (e.g., for controlling different devices and/or different instructions for control) to load control devices in the identified location. At 608, the example button press procedure 600 may end.

The system controller 110 may be configured to determine the location of a mobile device 182 and/or a remote control device 170 and react and/or respond when it is determined that the mobile device 182 and/or the remote control device 170 is in an authorized space (e.g., room, house, office building, etc.). As such, the system controller 110 may be configured to determine whether a device is attempting to control one of its control-target devices from an unauthorized location, for example, outside of a user's house, in an adjacent space or building, etc. The authorized spaces may be based on a user priority associated with the authorized space.

The system controller 110 may be configured to track occupants in restricted areas (e.g., using their mobile device 182). For example, if the system controller 110 determines that an occupant has entered a restricted area and/or is getting close to a restricted area, the system controller 110 may sound an alarm (e.g., visual, audio, etc.), indicate to the occupant that they are in a restricted area (e.g., flash the lights), provide a message via the occupant's mobile device 182, etc.

The system controller 110 may be configured to track occupants (e.g., via their mobile device 182) during an emergency. For example, the system controller 110 may be configured to determine whether any occupants are in a building during an emergency, and if so, what floors, rooms, etc. The system controller 110 may be configured to confirm whether or not all occupants are out of a space during an emergency situation. The system controller 110 may be configured to identify the number of occupants remaining in the space during the emergency situation.

The system controller 110 may be configured to calculate the utilization of different spaces (e.g., rooms) based on occupant tracking. For example, the system controller 110 may be configured to calculate the number of occupants (e.g., via their mobile device 182) in a space and/or the number of occupants in more than one space of a building over time. The system controller 110 may be configured to determine under and over utilized rooms based on this information. For example, this information may be further refined taking into consideration time of day, day of the week, etc. As such, the system controller 110 may be configured to determine whether additional space is desirable for the current occupants, whether particular spaces are being underutilized, etc.

The system controller 110 may be configured to determine the status of a hotel room based on information received from a mobile device 182. For example, a user may register their mobile device 182 with the hotel when checking in. The system controller 110 may be configured to determine whether the status of the user's hotel room (e.g., do not disturb, ready for service, unsold room) based on whether the mobile device 182 is in the room. The system controller 110 may indicate the hotel rooms that are "ready for service" based on a detection of the mobile device 182 within the room. For example, the system controller 110 may illuminate a light outside of the room, send a message to a mobile device 182 of the cleaning staff, etc.

The present application has been described with reference to the system controller 110 interacting between the control-source devices (e.g., the input devices) and the control-target devices (e.g., the load control devices). However, the control-source devices may transmit digital message directly to the control-target devices. In addition, while the present disclosure has been described with reference to the mobile device 182 and/or the input devices determining their locations, any of the control devices (e.g., including the load control devices) could be configured to determine its location. Further, the system controller 110 could be configured to determine the location of any of the control devices.

A control device of the system controller 110 (e.g., the load control devices, the input devices, and/or the mobile device 182) may be configured to use its location information during configuration of the load control system 100. For example, control devices that are located near each other may be configured to automatically associate with each other. When the mobile device 182 is being used to program and configure the operation of the load control system 100, the mobile device may use its present information to simplify the configuration procedure. The mobile device 182 may be configured to store the locations of each control device in the load control system. For example, the mobile device 182 may be configure to store the locations of remotely-located control devices (e.g., such as the LED drivers 130) that may be located out-of-view behind walls or above ceilings to provide for quick and easy location of the remotely-located control devices at a later date if the devices need to be serviced.

When the mobile device 182 is a wearable wireless device, the mobile device 182 may comprise one or more sensing devices for sensing one or more parameters (e.g., biometric data) that define the physical condition (e.g., behavior, movement, comfort, and/or health) of the occupant 180. For example, the mobile device 182 may comprise one or more sensing devices, such as but not limited to, an accelerometer for monitoring the movement of the occupant 180, an ambient light sensor for measuring the ambient light in the proximity of the occupant 180, a sound sensor (e.g., ambient noise sensor) for measuring the ambient noise in the proximity of the occupant 180, a temperature sensor (e.g., thermometer) for measuring the ambient temperature in the proximity of the occupant 180, a camera for measuring the pupil dilation of the occupant 180, the glare of the occupant 180, etc., a color temperature sensor for measuring color temperature of light sources (e.g., lighting loads 122 such as LED light sources 132, the sun, etc.), and/or sensors (e.g., electrodes) for measuring brainwaves of the occupant 180. The mobile device 182 may comprise sensing devices for monitoring the heart rate, the blood pressure, the body temperature, the blood sugar, breathing rate, breathing depth, and/or the perspiration level of the occupant 180. The mobile device 182 may be configured to transmit digital messages to the system controller 110 (e.g., as described herein) including data regarding the parameters measured by the sensing devices of the mobile device.

The system controller 110 may be configured to determine the state or physical condition of the occupant 180 using the parameters measured by the sensing devices of the mobile device 182. For example, the system controller 110 may be configured to determine that the occupant 180 is sleeping, the occupant 180 is falling asleep, the occupant 180 is waking up from sleep, the mood of the occupant 180, a relative stress level of the occupant 180 (e.g., that the stress level of the occupant 180 is increasing or decreasing), and/or the like in response to one or more of the parameters measured by the sensing devices of the mobile device 182. The occupant 180 may be determined to be sleeping when the system controller 110 determines that the occupant 180 has not moved or has moved less than a predefined amount within a defined period of time. The occupant 180 may be determined to be sleeping when the system controller 110 determines that the occupant 180 is in bed (e.g., for a predetermined period of time). The heart rate and/or breathing rate of the occupant 180 may also, or alternatively, be used to determine whether the occupant is sleeping (e.g., when the heart rate and/or breathing rate is below a predefined threshold for a defined period of time). The occupant 180 may be determined to be sleeping when the system controller 110 determines that the occupant 180 is snoring. Though specific indicators are provided for determining when the occupant 180 may be determined to be sleeping, any combination of these indicators and/or others may be used to determine the occupant is asleep.

The system controller 110 may be configured to control (e.g., automatically control) one or more load control devices (e.g., the dimmer switch 120, the LED drivers 130, the plug-in load control devices 140, the motorized window treatments 150, and/or the temperature control devices 160) and/or electrical loads in response to the parameters measured by the sensing devices of the mobile device 182. For example, the system controller 110 may be configured to turn on or off or adjust the intensity of the lighting loads 122 and/or the LED light sources 132 in response to the parameters measured by the sensing devices of the mobile device 182. The system controller 110 may be configured to adjust the color temperature of the LED light sources 132 in response to the parameters measured by the sensing devices of the mobile device 182. The system controller 110 may be configured to adjust the position of the motorized window treatments 150 in response to the parameters measured by the sensing devices of the mobile device 182. The system controller 110 may also be configured to adjust the setpoint temperature of the HVAC system 162 and/or turn a fan of the HVAC system on or off in response to the parameters measured by the sensing devices of the mobile device 182.

Figure 7:
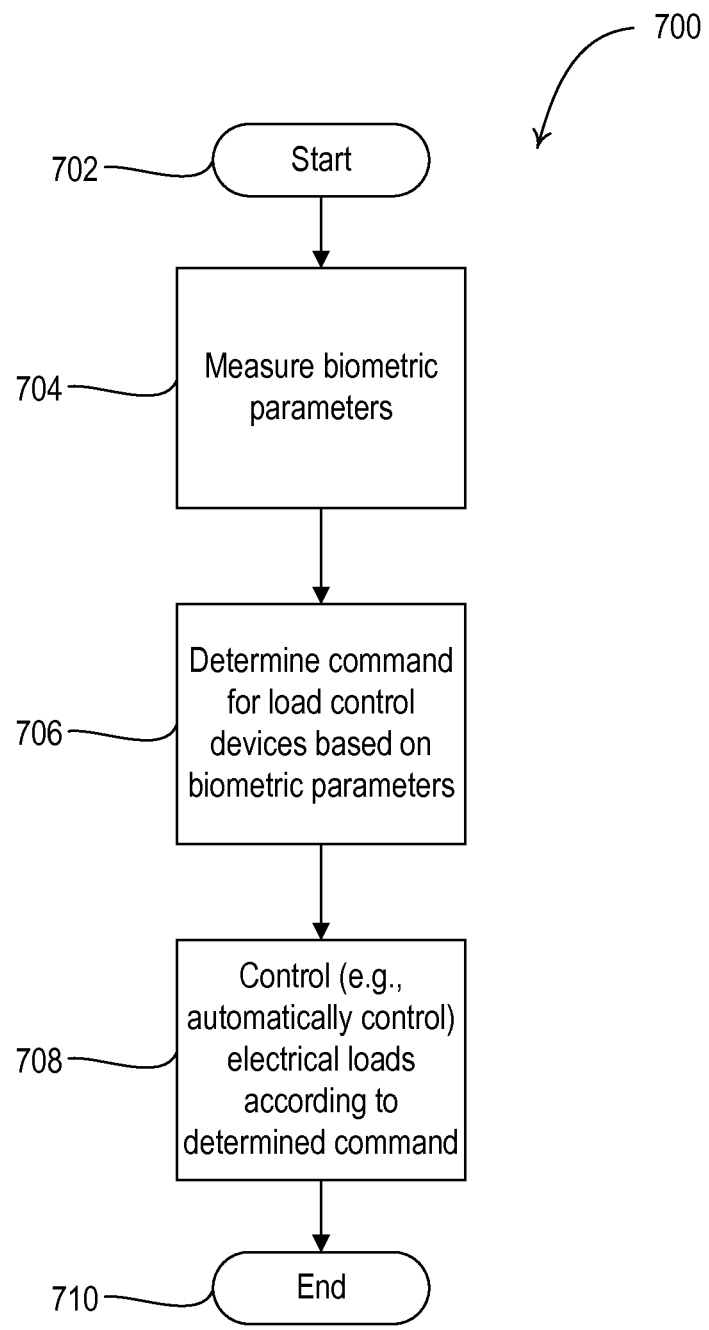
FIG. 7 is a flowchart of an example procedure for controlling electrical loads based on biometric parameters.

FIG. 7 is a flowchart of an example procedure 700 for controlling electrical loads based on biometric parameters. The procedure 700, or portions thereof, may be performed by the system controller 110, the mobile device 182, and/or one or more load control devices. The procedure 700 may start at 702. At 704, biometric parameters may be measured. The parameters may be measured by one or more sensor devices on the mobile device 182, or an external sensor, for example. The parameters may indicate the physical condition of an occupant 180. A command (e.g., load control instructions) may be determined at 706 for controlling one or more load control devices based on the biometric parameters. The one or more load control devices themselves may also be determined for being controlled based on the biometric parameters. The command and/or the load control devices for being controlled may be stored at the system controller 110 and/or the mobile device 182 and may be associated with the measured biometric parameters. The electrical loads may be controlled to attempt to adjust the physical condition of the occupant in response to the measured parameters.

At 708, the electrical loads may be controlled (e.g., automatically controlled) according to the determined command. For example, the system controller 110 or the mobile device 182 may send a digital message including the command to the load control device to automatically control the respective electrical load of the load control device in response to the measured parameters. The commands may also, or alternatively, be stored at the load control devices for being controlled. The load control devices may receive an indication of the measured parameters (e.g., from the system controller 110 or directly from the mobile device 182 or other sensor) and may execute the commands that correspond to the indicated parameters. The procedure 700 may end at 710. The control of a load control device and/or electrical load may be dependent upon the levels of the parameters measured by the sensing devices of the mobile device 182 (e.g., the exact stress level of the occupant 180, the heart rate of the occupant 180, etc.). The system controller 110 may determine how to control the load control devices and/or the electrical loads in response to the unique identifier of the mobile device 182, for example, in addition to one or more parameters measured by the sensing devices of the mobile device 182. For example, the unique identifier may indicate a medical condition of the occupant 180, such that the system controller 110 is able to appropriately control the load control devices and/or the electrical loads in response to the parameters measured by the sensing devices of the mobile device 182. The system controller 110 may associate the unique identifier with one or more presets (e.g., personalized settings) relating to lighting loads 122, the HVAC, motorized window treatments 150, etc.

The system controller 110 may be configured to control one or more load control devices and/or electrical loads in response to the parameters measured by the sensing devices of the mobile device 182 to attempt to adjust the state or physical condition of the occupant 180. For example, if the system controller 110 determines that the stress level of the occupant 180 is increasing (e.g., at a rate greater than a predetermined rate and/or above a predetermined threshold), the system controller 110 may be configured to decrease the intensity of the lighting loads 122, adjust the color temperature of the LED light sources 132 to a cooler color, open the motorized window treatments 150, decrease the setpoint temperature of the HVAC system 162, and/or cause the speaker 146 to play soothing music or sounds. For example, the mobile device 182 may determine the stress level and/or mood of the occupant 180 based on the tone of the occupant's voice, via a user input on the mobile device 182, the occupant's blood pressure, the occupant's heart rate, the occupant's body temperature, the occupant's breathing rate, the occupant's breathing depth, the occupant's perspiration level, and/or the like.

The system controller 110 may control one or more load control devices and/or electrical loads based on movement of the occupant 180 as determine by the mobile device 182. For example, if the system controller 110 determines that the occupant 180 is moving around the space, the system controller 110 may be configured to increase the intensity of the lighting loads 122 and/or decrease the setpoint temperature of the HVAC system 162. The system controller 110 may be configured to learn patterns of movement of the occupant 180. Using the learned patterns of movement and/or other sensed parameters of the occupant 180, the system controller 110 may predict the control of one or more load control devices and/or electrical loads. For example, the system controller 110 may learn that when waking from sleep at night (e.g., by identifying movement of the occupant 180 above a defined threshold after a period without movement), the occupant 180 usually travels to the bathroom, and as such, the system controller 110 may turn on a lighting load (e.g., to a low intensity level) in the bathroom before the occupant 180 reaches the space. The system controller 110 may determine that the occupant 180 is heading towards or away from home (e.g., or work, etc.) and control one or more loads in the occupant's house accordingly. For example, the system controller 110 may adjust the HVAC system, adjust the motorized window treatments to a preset level, turn on or off one or more loads (e.g., lighting loads), play music, etc.

The system controller 110 may determine an occupant's action based on one or more parameters measured by the sensing devices of the mobile device 182 and control one or more load control devices and/or electrical loads accordingly. For example, the system controller 110 may determine that the occupant is reading based on the mobile device 182 (e.g., based on the occupant's gaze point as determined by the mobile device 182), and may control one or more lighting loads 122 and/or motorized window treatments 150 to ensure proper light levels for reading are provided (e.g., by measuring the light levels at the surface where the occupant 180 is looking). The system controller 110 may determine the occupant's gaze point using a camera located on the mobile device 182 (e.g., smart glasses), the level of sun glare, the ambient light level, the color temperature of the light, etc., and adjust one or more load control devices and/or electrical loads accordingly. For example, the system controller 110 may use the mobile device 182 to determine where the occupant 180 is looking (e.g., the direction the occupant 180 is looking), and determine a load control device and/or electrical load at which the occupant 180 is looking. The system controller 110 may configure that load control devices and/or electrical load accordingly, for example, to configure the load control device and/or electrical load for the load control system 100 (e.g., commission the load control device and/or electrical load into the load control system 100). For example, the system controller 110 may adjust the intensity of a lighting load and/or the shade level in the direction an occupant 180 is looking to decrease or increase the amount of light in the direction the occupant 180 is looking. The system controller 110 may adjust the color temperature of a lighting load in the direction the occupant 180 is looking to make the color temperature warmer or cooler in the direction the occupant 180 is looking. For example, the system controller 110 may display a cooler color temperature when the occupant 180 is reading or trying to stay awake, and/or a warmer color temperature when the occupant 180 is trying to fall asleep. The presets may be stored at the system controller 110 for being implemented upon a user indication (e.g., a reading mode, a sleep mode, or a stay awake mode). The system controller 110 may also adjust the setpoint temperature of the HVAC unit (e.g., to a lower temperature) and/or the intensity of the lights (e.g., to an increased lighting level) when the occupant 180 is trying to stay awake.

The system controller 110 may control one or more load control devices and/or electrical loads based on predefined movements (e.g., gestures) of the occupant 180 as determine by the mobile device 182 and/or the system controller 110. For example, the system controller 110 may determine that the occupant 180 is moving their hand and/or arm in a particular manner (e.g., waving, raising, lowering, etc.) and control one or more load control devices and/or electrical loads accordingly (e.g., turn on/off, raise the intensity, lower the intensity, etc.).

The system controller 110 may be configured to control the load control devices and/or the electrical loads to save energy in response to the parameters measured by the sensing devices of the mobile device 182. The system controller 110 may be configured to determine that the occupant 180 has just fallen asleep (e.g. is asleep less than a predetermined period of time) in response to the parameters measured by the sensing devices of the mobile device 182 and to turn off and/or reduce the amount of power delivered to one or more of the electrical loads (e.g., the HVAC system 162, one or more lighting loads 122, one or more motorized window treatments 150, an appliance such as a television, and/or the like).

The system controller 110 may be configured to control the load control devices and/or electrical loads in response to determining that the occupant 180 is asleep or awake. The system controller 110 may be configured to determine whether the occupant is asleep, is awake, has just fallen asleep (e.g., within a predetermined period of time), and/or has just awaken from being asleep based on the parameters measured by the sensing devices of the mobile device 182, the time of day, and/or the location of the occupant 180. The system controller 110 may determine that the occupant is awake when the occupant is determined not to be asleep. The system controller 110 may determine that the occupant has just awaken when the occupant 180 has been determined to be asleep (e.g., for a predetermined period of time) and then is determined to be awake for a predetermined period of time since being asleep.

The system controller 110 may be configured to determine parameters of the occupant 180 while they are asleep based on the parameters measured by the sensing devices of the mobile device 182. The system controller 110 may be configured to determine that the occupant 180 is starting to fall asleep and reduce the amount of power delivered to one or more of the electrical loads (e.g., such as turning off the lighting loads 122, reducing the lighting level of the lighting loads 122, turning off or turning down the television 144, turning off or turning down a radio, etc.), adjust one or more motorized window treatments 150, and/or adjust the color temperature of one or more lighting loads 122, which for example, may assist the occupant 180 in falling asleep. For example, the color temperature of one or more lighting loads 122 may be changed to a warmer color (e.g., more red in color) to assist the occupant 180 in falling asleep. The system controller 110 may be configured to determine that the occupant 180 has fallen asleep and to turn off and/or reduce the amount of power delivered to one or more of the electrical loads (e.g., such as turning off the lighting loads 122, the television 144, a radio, etc.).

The system controller 110 may be able to determine that the occupant 180 is asleep and is starting to wake up and increase (e.g., slowly increase) the intensity of the lighting loads 122, adjust the color temperature of the LED light sources 132, raise the motorized window treatments 150, and/or adjust the HVAC system, for example, to improve the experience of the occupant 180 while waking up. For example, the system controller 110 may control one or more lighting loads 122 and/or motorized window treatments 150 in the vicinity of the occupant 180 based on the circadian rhythm of the occupant 180, for example, based on ambient light levels and/or spectral light information gathered via the mobile device 182, based on biometric data of the occupant 180, based on sleep patterns of the occupant 180, etc. The system controller 110 may be able to determine that the occupant 180 is in need of sleep based on the parameters measured by the sensing devices of the mobile device 182, and in response, encourage sleep by alerting the user and/or decreasing the intensity of the lighting loads 122, adjusting the color temperature of the LED light sources 132 to a warmer color, lowering the motorized window treatments 150, and/or adjusting (e.g., lowering or raising) the HVAC system. The system controller 110 may determine that the occupant 180 is in need of sleep after a predetermined amount of time has elapsed since the occupant 180 was determined to be asleep, when the occupant 180 is in bed and not determined to be asleep, is determined to fall asleep for multiple short (e.g., predetermined) periods of time within a timeframe, is awake after a predetermined time, is awake after a predetermined time on certain days of the week (e.g., weekdays), is awake after a predetermined time with an event on the calendar of the mobile device 182 the next day, or any combination thereof.

The system controller 110 may be configured to adjust the HVAC system 162 based on the parameters measured by the sensing devices of the mobile device 182, the time of day, and/or the location of the occupant 180. The system controller 110 may be configured to control HVAC system 162 by adjusting the temperature set point of the HVAC system 162, air flow of the HVAC system 162 (e.g., via damper control), radiant heating of the HVAC system 162, fans (e.g., ceiling fans, fans of the HVAC system 162, etc.), motorized window treatments 150, lighting loads 122, and/or the like. For example, the system controller 110 may be configured to adjust the HVAC system 162 based on the body temperature of the occupant 180 to ensure comfort of the occupant (e.g., while the occupant 180 is sleeping). If the system controller 110 determines that the occupant 180 has a high heart rate (e.g., based on the biometric parameters because the occupant was running), the system controller 110 may turn down the temperature set point of the HVAC system.

The system controller 110 may be configured to control (e.g., automatically control) one or more load control devices and/or electrical loads based on information from one or more of an application running on the mobile device 182, one or more parameters (e.g., biometric data) that define the physical condition of the occupant 180, the time of day, and/or the location of the occupant 180. As such, the system controller 110 may determine what the occupant 180 is currently doing, was doing, or is about to do, and control one or more load control devices and/or electrical loads accordingly. For example, the system controller 110 may determine that the occupant 180 initiates an input of a mobile application running on the mobile device 182 and the location of the occupant 180. The mobile application may comprise, for example, a movie/television application (e.g., Netflix®, Apple TV® mobile app, etc.), a workout application, a utility application, etc. Based on this determination, for example in combination with a parameter (e.g., biometric data) that defines the physical condition of the occupant 180, the time of day, and/or the location of the occupant 180, the system controller 110 may control one or more load control devices and/or electrical loads accordingly.

For example, if the application comprises a movie/television application and the occupant initiates the play of a movie or television show, the system controller 110 may adjust an intensity of one or more lights in the proximity of the occupant 180 to a movie watching mode (e.g., a low intensity level). If the system controller 110 determines that the occupant 180 has pressed stop or pause using the application, the system controller 110 may raise the light level of the lights and/or a shade level of a motorized window treatment (e.g., in the same room and/or an adjacent room), for example, such that the occupant 180 may have more light to get up and walk around (e.g., in the room or an adjacent room such as the kitchen or bathroom). The mobile application may comprise a utility application, such as a flashlight application, for example. If the system controller 110 determines that the occupant 180 has initiated a flashlight application on their mobile device 182 at night, the system controller 110 may not turn on lights it is otherwise programmed to turn on, for example, because the occupant 180 might not want to wake up a guest.

The system controller 110 may be configured to control (e.g., automatically control) one or more load control devices and/or electrical loads to provide an alert, an alarm, or a warning in response to the parameters measured by the sensing devices of the mobile device 182. For example, the system controller 110 may be configured to blink the lighting loads 122, display a message on the display of the mobile device 182 of the occupant 180 or the mobile device 182 of a caregiver, provide an alarm (e.g., audio alarm, vibration, etc.) using the mobile device 182 of the occupant 180 or the mobile device 182 of the caregiver, and/or generate an alarm with the speaker 146 in the vicinity of the occupant 180 and/or the caregiver of the occupant 180. For example, the system controller 110 may be configured to determine and/or predict an abnormal condition with the occupant 180 (e.g., while the occupant 180 is sleeping), and to blink the lighting loads 122 and/or generate an alarm (e.g., with the speaker 146 in the vicinity of a caregiver of the occupant 180). The system controller 110 may be configured to blink the lighting loads 122 and/or adjust the color temperature of the LED light sources 132 in the vicinity of the occupant 180 to indicate the location of the occupant 180 to the caregiver. The system controller 110 may be configured to blink the lighting loads 122 and/or generate an alarm in response to a warning or information received via the Internet. The system controller 110 may be configured to increase the intensity of a lighting load 122 to provide a subtle alert to the occupant 180. The system controller 110 may be configured to blink the lighting load 122 instead of ringing a doorbell, for example, during certain times of day (e.g., at night). For example, the system controller 110 may blink the lighting load 122 that is in closest proximity to the occupant 180.

If there are multiple occupants in a single room, the system controller 110 may be configured to control (e.g., automatically control) one or more load control devices and/or electrical loads using a predetermined priority (e.g., a tiered hierarchy) of occupants 180. For example, the system controller 110 may control (e.g., automatically control) a load control device in response to the parameters measured by the sensing devices of the mobile device 182 in the room that has the highest priority. The priorities and/or tiered hierarchy may be determined during a configuration procedure of the load control system 100 and may be stored in memory in the system controller 110. The priority and/or tiered hierarchy may be based on an occupant type and/or individual occupants within a space.

The occupant 180 may be a parent, a child, an elderly person, or a pet, each of which may be assigned with a mobile device 182. Each occupant 180 may be identified with an occupant type that indicates the type of occupant and/or a unique occupant identifier that uniquely identifies the occupant. The system controller 110 may use the occupant type and/or the occupant identifier for controlling devices in the vicinity of the occupant 110. As such, the system controller 110 may be configured to monitor the child, elderly person, or pet based on one or more parameters measured by the sensing devices of their respective mobile device 182. For example, the system controller 110 may be configured to turn on a lighting load 122 (e.g., slowly turn on the lighting load 122) in proximity to a parent when the child starts to wake up, for example, to alert the parent. The system controller 110 may be configured to turn on a lighting load 122 in the child's bedroom, hallway, and/or bathroom if the system controller 110 determines that the child wakes up during the night. The system controller 110 may be configured to turn on or blink a lighting load 122 in the parent's bedroom if the system controller 110 determines that the child wakes up during the night. Appliances in the house may have different alerts based on the system controller 110 determining whether the child is awake or not. For example, if the doorbell is actuated and the system controller 110 determines that the child is sleeping, the system controller 110 may blink a lighting load 122 in proximity to an occupant 180 as opposed to ringing the doorbell.

The system controller 110 may be configured to determine one or more parameters of a pet based on measurements of the sensing devices of the mobile device 182 of the pet. The system controller 110 may determine that the pet is at a particular location (e.g., at a back door and in need of going outside), and alert an occupant 180 (e.g., the owner of the pet) by blinking a lighting load 122 in proximity to the occupant 180. The system controller 110 may determine the location of the pet (e.g., based on the pet's mobile device 182 or the camera device 176), and when the pet is near (e.g., within a predetermined distance of) a pet door, open the pet door for the pet. The system controller 110 may determine the location of the pet (e.g., based on the pet's mobile device 182 or the camera device 176), and when the pet is near (e.g., within a predetermined distance of) a window, open the window shades via the respective motorized window treatment.

The system controller 110 may be configured to determine that the occupant 180 is working out too strenuously (e.g., based on a heart rate above a threshold), and alert the occupant 180, for example, by blinking a lighting load 122 in proximity to the occupant 180. For example, the system controller 110 may blink the lighting loads 122 in a room or a portion of lighting loads in the room in which the occupant is working out. The threshold may be set by the occupant 180 or another user.

The system controller 110 may be configured to collect data throughout a building based on one or more parameters measured by the sensing devices of the mobile device 182. The combined parameters from multiple sensors may be used by the system controller 110 to provide make a determination and/or provide an indication. For example, the system controller 110 may collect data relating to HVAC usage, lighting usage, occupant settings, travel and/or usage patterns, and/or the like. The system controller 110 may map temperature throughout a building using the sensors of one or more mobile devices 182 (e.g., mobile devices of a user traveling throughout the building and/or multiple users throughout the building). The system controller 110 may identify the current lighting levels in the rooms throughout the building using the parameters measured by one or more mobile devices 182. If multiple microphones hear a sound, the volume of the sound may be used to determine the location of the source of the sound relative to the location of the microphones. If multiple temperature sensors detect a change in temperature, the relative change in temperature and the location of the temperature sensors may be used to determine the location of the source of the temperature change relative to the location of the temperature sensors.

Figure 8:
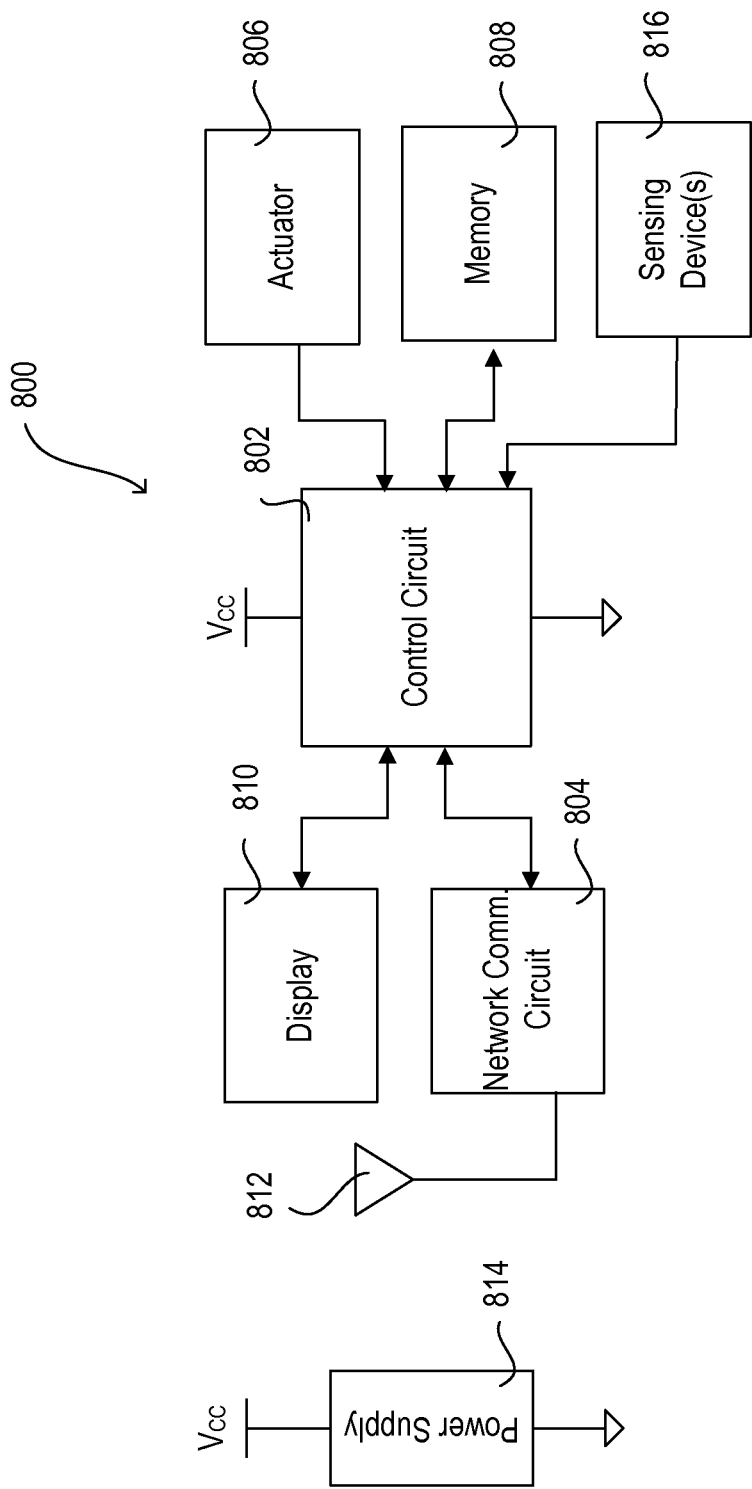
FIG. 8 is a simplified block diagram of an example network device.

FIG. 8 is a block diagram illustrating an example network device 800. The network device 500 may be a mobile device, such as the mobile device 182 shown in FIG. 1 for example, or another computing device. The network device 800 may be a personal computer (e.g., personal computer 164), a server, a laptop, a tablet, a smart phone, a control-source device (e.g., an input device), and/or other suitable network communication device (e.g., an Internet-Protocol-enabled device), for example. The network device 800 may be a wearable device. Examples of wearable wireless devices may include an activity tracking device (e.g., such as a FitBit® device, a Misfit® device, and/or a Sony Smartband® device), a smart watch, smart clothing (e.g., OMsignal® smartwear, etc.), and/or smart glasses (e.g., such as Google Glass® eyewear). The network device 800 may perform the functions of a control-source device (e.g., input device) in the load control system 100.

The network device 800 may comprise a control circuit 802, which may include one or more of a processor (e.g., a microprocessor), a microcontroller, a programmable logic device (PLD), a field programmable gate array (FPGA), an application specific integrated circuit (ASIC), or any suitable processing device. The control circuit 802 may perform signal coding, data processing, power control, image processing, input/output processing, and/or any other functionality that enables the network device 800 to perform as described herein.

The control circuit 802 may store information in and/or retrieve information from the memory 808. The memory 808 may include a non-removable memory and/or a removable memory for storing computer-readable media. The non-removable memory may include random-access memory (RAM), read-only memory (ROM), a hard disk, and/or any other type of non-removable memory storage. The removable memory may include a subscriber identity module (SIM) card, a memory stick, a memory card (e.g., a digital camera memory card), and/or any other type of removable memory. The control circuit 802 may access the memory 808 for executable instructions and/or other information that may be used by the network device 800. The control circuit 802 may access instructions in the memory 808 for performing as described herein.

The network device 800 may comprise a network communication circuit 804, which may be adapted to perform wired and/or wireless communications (e.g., with the system controller 110 or another device over a network) on behalf of the network device 800. The network communication circuit 804 may be a wireless communication circuit, for example, including an RF transceiver coupled to an antenna 812 for transmitting and/or receiving RF signals. The network communication circuit 804 may communicate using Wi-Fi, a proprietary protocol (e.g., the ClearConnect® protocol), Bluetooth®, or any other RF communications. The control circuit 802 may be coupled to the network communication circuit 804 for transmitting and/or receiving digital messages via the RF signals, for example.

The network device 800 may comprise an actuator 806. The control circuit 802 may be responsive to the actuator 806 for receiving a user input. For example, the control circuit 802 may be operable to receive a button press from a user on the network device 800 for making a selection or performing other functionality on the network device 800. The control circuit 802 may be responsive to receiving other user input (e.g., via software and/or actuation of a soft button on a display).

The network device 800 may comprise a display 810. The control circuit 802 may be in communication with a display 810 for displaying information to a user. The communication between the display 810 and the control circuit 802 may be a two way communication, as the display 810 may include a touch screen module capable of receiving information from a user and providing such information to the control circuit 802.

The control circuit 802 may sense information using the one or more sensing devices 818. The sensing devices 818 may sense one or more parameters (e.g., biometric data) that define the physical condition (e.g., behavior, movement, comfort, and/or health) of an occupant. For example, the sensing devices 818 may include an accelerometer for monitoring the movement of the occupant, devices for monitoring heart rate, devices for monitoring blood pressure, devices for monitoring body temperature, devices for monitoring blood sugar, and/or devices for monitoring perspiration level of an occupant. The parameters may be stored in and/or retrieved from the memory 808. The control circuit 802 may transmit digital messages including the parameters and/or data regarding the parameters measured by the sensing devices 818 via the network communication circuit 804.

The network device 800 may comprise a power supply 814 for generating a DC supply voltage $V_{CC}$ for powering the control circuit 802, the network communication circuit 804, the memory 808, the display 810, the one or more sensing devices 818, and/or other circuitry of the network device 800. The power supply 814 may be a battery or another source of power for the network device 800.

Figure 9:
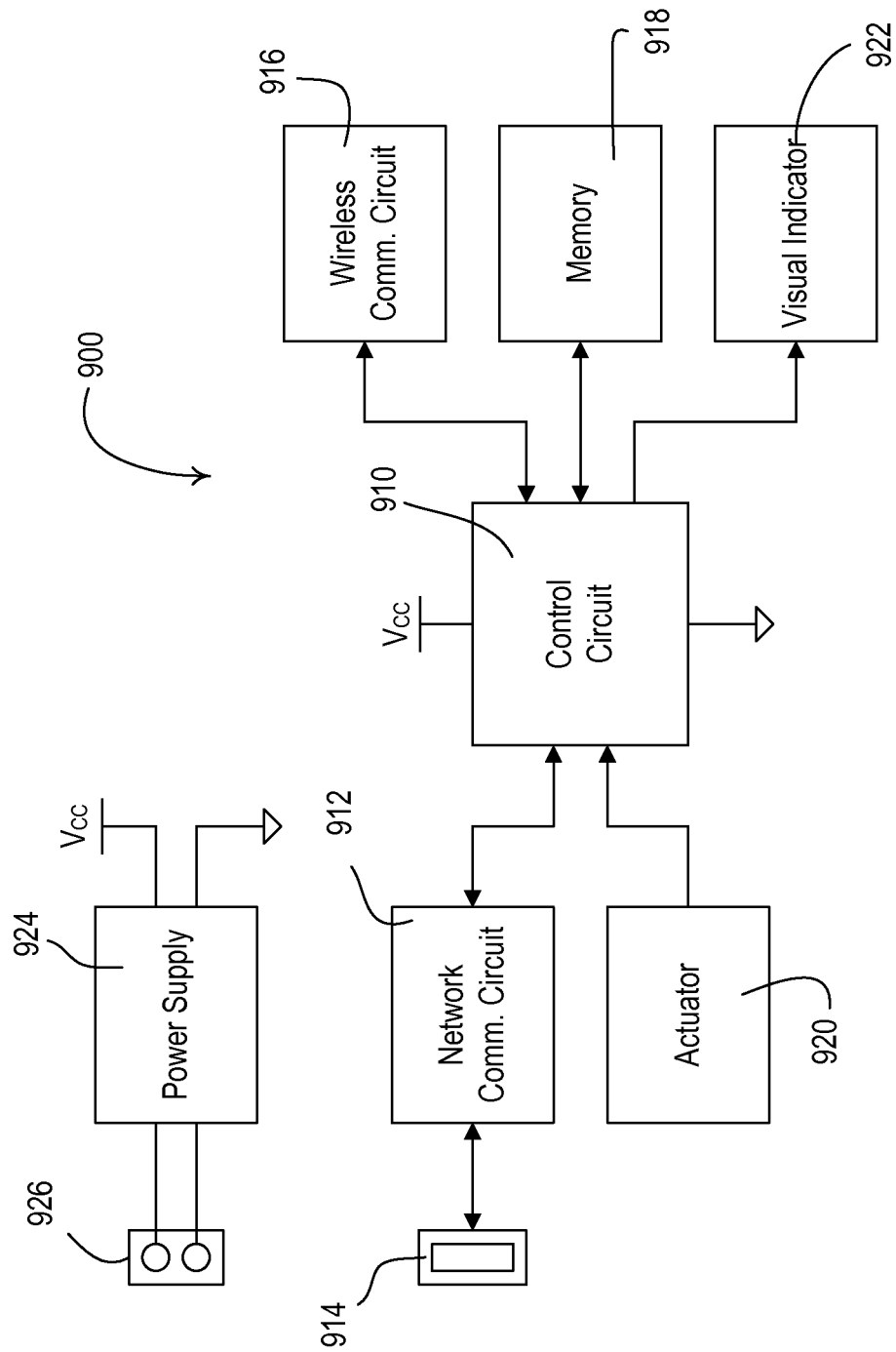
FIG. 9 is a simplified block diagram of an example system controller.

FIG. 9 is a simplified block diagram of an example system controller 900, which may be deployed as, for example, the system controller 110 of the load control system 100 shown in FIG. 1. The system controller 900 may comprise a control circuit 910, which may include one or more of a processor (e.g., a microprocessor), a microcontroller, a programmable logic device (PLD), a field programmable gate array (FPGA), an application specific integrated circuit (ASIC), or any suitable processing device. The control circuit 910 may perform signal coding, data processing, power control, input/output processing, and/or any other functionality that enables the system controller 900 to perform as described herein.

The system controller 900 may comprise a network communication circuit 912 that may be capable of performing wired and/or wireless communications. The network communication circuit may be coupled to a network connector 914 (e.g., an Ethernet jack), which may be adapted to be connected to a wired digital communication link (e.g., an Ethernet communication link) for allowing the control circuit 910 to communicate with network devices on a network. The network communication circuit 912 may be configured to be wirelessly connected to the network, e.g., using Wi-Fi technology or other protocols to transmit and/or receive RF signals.

The system controller 900 may comprise a wireless communication circuit 916, for example, including an RF transceiver coupled to an antenna for transmitting and/or receiving RF signals. The wireless communication circuit 916 may communicate using a proprietary protocol (e.g., the ClearConnect® protocol). The control circuit 910 may be coupled to the wireless communication circuit 916 for transmitting digital messages via the RF signals, for example, to control the load control devices in the load control system 100 in response to digital messages received via the network communication circuit 912. The control circuit 910 may be configured to send/receive digital messages, for example, to/from the load control devices and/or the input devices via the wireless communication circuit 916.

The control circuit 910 may be responsive to an actuator 920 for receiving a user input. For example, the control circuit 910 may be operable to associate the system controller 900 with one or more control devices of the load control system 100 in response to actuations of the actuator 920 during a configuration procedure of the load control system 100. The system controller 900 may comprise additional actuators to which the control circuit 910 may be responsive.

The control circuit 910 may store information in and/or retrieve information from the memory 918. The memory 918 may include a non-removable memory and/or a removable memory for storing computer-readable media. The non-removable memory may include random-access memory (RAM), read-only memory (ROM), a hard disk, and/or any other type of non-removable memory storage. The removable memory may include a subscriber identity module (SIM) card, a memory stick, a memory card (e.g., a digital camera memory card), and/or any other type of removable memory. The control circuit 910 may access the memory 918 for executable instructions and/or other information that may be used by the system controller 900 to perform as described herein.

The control circuit 910 may illuminate a visual indicator 922 to provide feedback to a user of the load control system 100. For example, the control circuit 910 may blink or strobe the visual indicator 922 to indicate a fault condition. The control circuit 910 may be operable to illuminate the visual indicator 922 different colors to indicator different conditions or states of the system controller 900. The visual indicator 922 may be illuminated by, for example, one or more light-emitting diodes (LEDs). The system controller 900 may comprise more than one visual indicator.

The system controller 900 may comprise a power supply 924 for generating a DC supply voltage $V_{CC}$ for powering the control circuit 910, the network communication circuit 912, the wireless communication circuit 916, the memory 918, the visual indicator 922, and/or other circuitry of the system controller 900. The power supply 924 may be coupled to a power supply connector 926 (e.g., a USB port) for receiving a supply voltage (e.g., a DC voltage) and/or for drawing current from an external power source.

Figure 10:
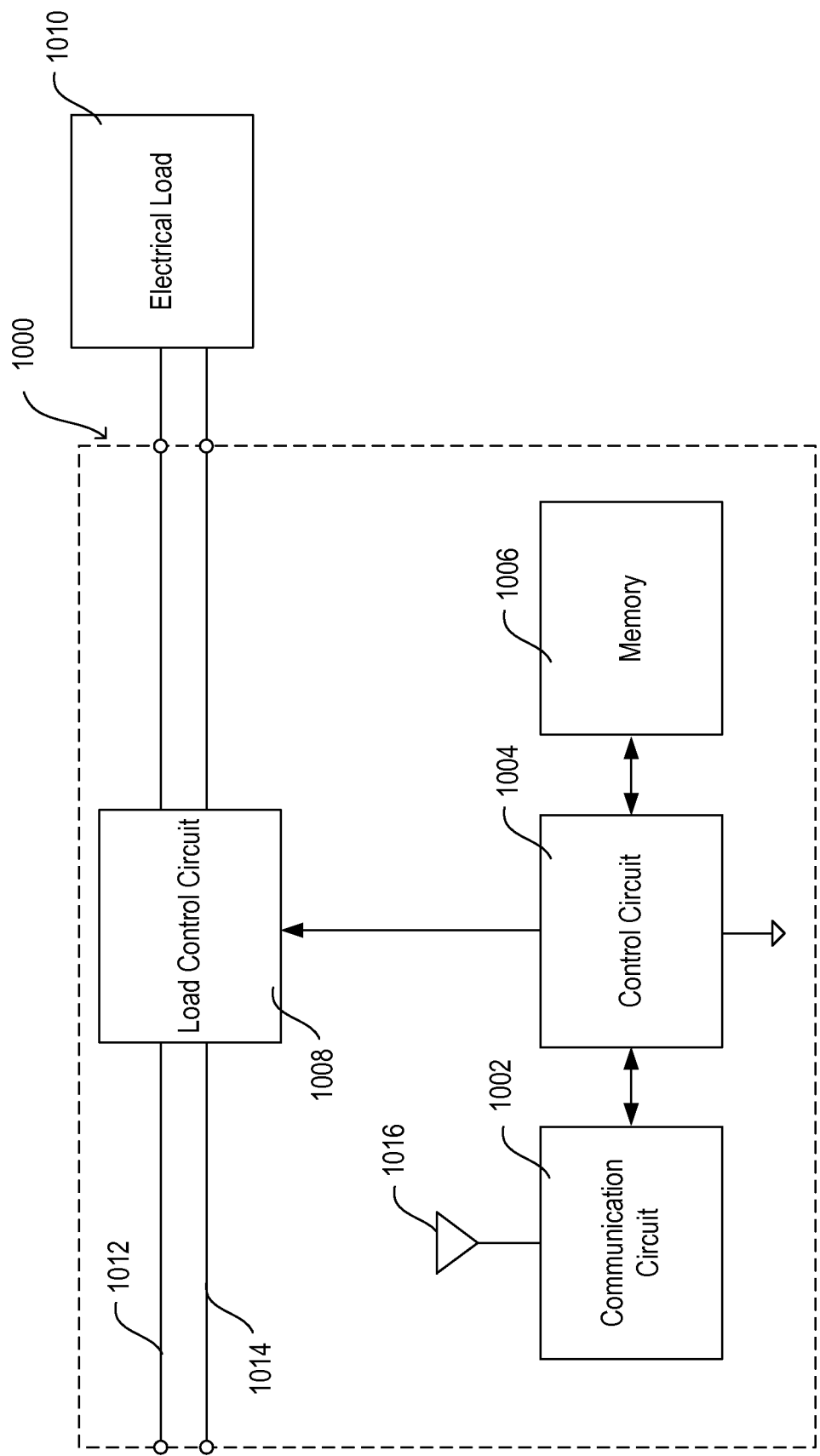
FIG. 10 is a simplified block diagram illustrating an example control device.

FIG. 10 is a block diagram illustrating an example load control device 1000. The load control device 1000 may be a control-source device and/or a control-target device for example. The load control device 1000 may be a dimmer switch, an electronic switch, an electronic ballast for lamps, an LED driver for LED light sources, a plug-in load control device, a temperature control device (e.g., a thermostat), a motor drive unit for a motorized window treatment, or other load control device. The load control device 1000 may include a communication circuit 1002. The communication circuit 10002 may include a receiver, an RF transceiver or other communication module capable of performing wired and/or wireless communications. The wireless communications may be sent/received via an antenna 1016.

The communication circuit 1002 may be in communication with a control circuit 1004. The control circuit 1004 may include one or more general purpose processors, special purpose processors, conventional processors, digital signal processors (DSPs), microprocessors, integrated circuits, a programmable logic device (PLD), application specific integrated circuits (ASICs), or the like. The control circuit 1004 may perform signal coding, data processing, power control, input/output processing, or any other functionality that enables the load control device 1000 to perform as described herein.

The control circuit 1004 may store information in and/or retrieve information from a memory 1006. For example, the memory 1006 may maintain device identifiers of associated devices and/or instructions that may be executed by the control circuit 1004 for performing as described herein. The memory 1006 may include a non-removable memory and/or a removable memory. The load control circuit 1008 may receive instructions from the control circuit 1004 and may control the electrical load 1010 based on the received instructions. The load control circuit 1008 may receive power via the hot connection 1012 and the neutral connection 1014 and may provide an amount of power to the electrical load 1010. The electrical load 1010 may include any type of electrical load.

Although features and elements are described above in particular combinations, each feature or element can be used alone or in any combination with the other features and elements. The methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), removable disks, and optical media such as CD-ROM disks, and digital versatile disks (DVDs).

What is claimed is:

1. A load control system, comprising:
one or more control-source devices;
one or more control-target devices, each of the one or more control-target devices operatively couplable to a respective one of one or more electrical load devices disposed in a space;
a system controller communicatively coupled to the one or more control-source devices and to the one or more control-target devices via a first network using a first network protocol, the system controller to:
receive, via the first network using the first network protocol, data representative of an occupant within the space;
receive, from a mobile device associated with the occupant of the space via a second network using a second network protocol different from the first network protocol, data representative of:
one or more biometric parameters associated with the occupant in the space; and
a unique identifier associated with the mobile device;
determine one or more output parameters for each of at least one of the one or more electrical load devices using the received unique identifier and the received data representative of the one or more biometric parameters associated with the occupant in the space; and
communicate, via the first network using the first network protocol, the one or more determined output parameters to the control-target device associated with each respective one of the one or more electrical load devices.

2. The load control system of claim 1, the system controller to further:
receive from the mobile device, data indicative of initiation of an application on the mobile device; and
determine the one or more output parameters for each of the at least one of the one or more electrical load devices using:
the received data representative of the initiation of the application;
the received data representative of the one or more biometric parameters associated with the occupant in the space; and
the unique identifier of the mobile device.

3. The load control system of claim 1, the system controller to further:
receive from the mobile device, data indicative of one or more medical conditions associated with the occupant of the space; and determine the one or more output parameters for each of the at least one of the one or more electrical load devices using:
the received data representative of the one or more medical conditions of the occupant of the space;
the received data representative of the one or more biometric parameters associated with the occupant in the space; and
the unique identifier of the mobile device.

4. The load control system of claim 3, the system controller to further:
determine whether at least one of the one or more biometric parameters associated with the occupant of the space falls outside a predetermined range of allowable biometric parameter values based on the data representative of the one or more medical conditions associated with the occupant of the space; and
determine one or more alert output parameters for each of at least one of the one or more electrical load devices responsive to the determination that at least one of the one or more biometric parameters associated with the occupant of the space falls outside the predetermined range of allowable biometric parameter values; and
communicate, via the first network, the one or more determined alert output parameters to the control-target device associated with each respective one of the one or more electrical load devices.

5. The load control system of claim 1 wherein the data representative of the one or more biometric parameters includes data indicative of one or more gestures by the occupant of the space.

6. The load control system of claim 5 wherein at least one of the one or more control-source devices provides, via the first network, at least a portion of the data indicative of the one or more gestures by the occupant of the space.

7. The load control system of claim 5 wherein the mobile device associated with the occupant of the space provides, via the second network, at least a portion of the data indicative of the one or more gestures by the occupant of the space.

8. The load control system of claim 1 wherein the one or more electrical load devices include one or more lamps; and
wherein to determine the one or more output parameters for each of the at least one of the one or more electrical load devices using the received data representative of the one or more biometric parameters associated with the occupant in the space, the control system to further:
determine an output luminous intensity for each of the one or more lamps using the received data representative of the one or more biometric parameters associated with the occupant in the space.

9. The load control system of claim 1 wherein the one or more electrical load devices include one or more lamps; and
wherein to determine the one or more output parameters for each of the at least one of the one or more electrical load devices using the received data representative of the one or more biometric parameters associated with the occupant in the space, the control system to further:
determine an output color temperature for each of the one or more lamps using the received data representative of the one or more biometric parameters associated with the occupant in the space.

10. The load control system of claim 1 wherein the one or more electrical load devices include one or more lamps; and
wherein to determine the one or more output parameters for each of the at least one of the one or more electrical load devices using the received data representative of the one or more biometric parameters associated with the occupant in the space, the control system to further:
determine an output color spectrum for each of the one or more lamps using the received data representative of the one or more biometric parameters associated with the occupant in the space.

11. The load control system of claim 1 wherein the one or more electrical load devices include one or more motorized window coverings; and
wherein to determine the one or more output parameters for each of the at least one of the one or more electrical load devices using the received data representative of the one or more biometric parameters associated with the occupant in the space, the control system to further:
determine an output position for each of the one or more motorized window coverings using the received data representative of the one or more biometric parameters associated with the occupant in the space.

12. A system controller communicatively couplable to one or more control-source devices and one or more control-target devices operatively couplable to a respective one of one or more electrical load devices disposed in a space, the system controller comprising:
first communications interface circuitry to communicatively couple to a first network using a first network protocol;
second communications interface circuitry to communicatively couple to a second network using a second network protocol different from the first network protocol;
processor circuitry communicatively coupled to the first communications interface circuitry and to the second communications interface circuitry, the processor circuitry to:
receive, via the first communications interface circuitry, data representative of an occupant within the space;
receive, from a mobile device associated with the occupant of the space via the second communications interface circuitry, data representative of:
one or more biometric parameters associated with the occupant in the space; and
a unique identifier associated with the mobile device;
determine one or more output parameters for each of at least one of the one or more electrical load devices using the received unique identifier and the received data representative of the one or more biometric parameters associated with the occupant in the space; and
communicate, via the first network using the first network protocol, the one or more determined output parameters to the control-target device associated with each respective one of the one or more electrical load devices.

13. The system controller of claim 12, the processor circuitry to further:
receive from the mobile device, via the second communications interface circuitry, data indicative of initiation of an application on the mobile device; and
determine the one or more output parameters for each of the at least one of the one or more electrical load devices using:
the received data representative of the initiation of the application;

the received data representative of the one or more biometric parameters associated with the occupant in the space; and the received unique identifier.

14. The system controller of claim 12, the processor circuitry to further:

receive from the mobile device, via the second communications interface circuitry, data indicative of one or more medical conditions associated with the occupant of the space; and determine the one or more output parameters for each of the at least one of the one or more electrical load devices using:

the received data representative of the one or more medical conditions of the occupant of the space;

the received data representative of the one or more biometric parameters associated with the occupant in the space; and the received unique identifier.

15. The system controller of claim 14, the processor circuitry to further:

determine whether at least one of the one or more biometric parameters associated with the occupant of the space falls outside a predetermined range of allowable biometric parameter values based on the data representative of the one or more medical conditions associated with the occupant of the space; and determine one or more alert output parameters for each of at least one of the one or more electrical load devices responsive to the determination that at least one of the one or more biometric parameters associated with the occupant of the space falls outside the predetermined range of allowable biometric parameter values; and communicate, via the first network, the one or more determined alert output parameters to the control-target device associated with each respective one of the one or more electrical load devices.

16. The system controller of claim 12 wherein to receive the data representative of one or more biometric parameters associated with the occupant in the space, the processor circuitry to further:

receive data indicative of one or more gestures by the occupant of the space.

17. The system controller of claim 16 wherein to receive data indicative of the one or more gestures by the occupant of the space, the processor circuitry to further:

receive, from at least one of the one or more control-source devices via the first communications interface circuitry, at least a portion of the data indicative of the one or more gestures by the occupant of the space.

18. The system controller of claim 16 wherein to receive data indicative of the one or more gestures by the occupant of the space, the processor circuitry to further:

receive, from the mobile device associated with the occupant of the space via the second communications interface circuitry, at least a portion of the data indicative of the one or more gestures by the occupant of the space.

19. The system controller of claim 12 wherein to determine the one or more output parameters for each of the at least one of the one or more electrical load devices using the received data representative of the one or more biometric parameters associated with the occupant in the space, the processor circuitry to further:

determine a respective output luminous intensity for each of one or more lamps using the received data representative of the one or more biometric parameters associated with the occupant in the space.

20. The system controller of claim 12 wherein to determine the one or more output parameters for each of the at least one of the one or more electrical load devices using the received data representative of the one or more biometric parameters associated with the occupant in the space, the processor circuitry to further:

determine a respective output color temperature for each of one or more lamps using the received data representative of the one or more biometric parameters associated with the occupant in the space.

21. The system controller of claim 12 wherein to determine the one or more output parameters for each of the at least one of the one or more electrical load devices using the received data representative of the one or more biometric parameters associated with the occupant in the space, the processor circuitry to further:

determine a respective output color spectrum for each of one or more lamps using the received data representative of the one or more biometric parameters associated with the occupant in the space.

22. The system controller of claim 12 wherein to determine the one or more output parameters for each of the at least one of the one or more electrical load devices using the received data representative of the one or more biometric parameters associated with the occupant in the space, the processor circuitry to further:

determine a respective output position for each of one or more motorized window coverings using the received data representative of the one or more biometric parameters associated with the occupant in the space.

23. A non-transitory, machine-readable, storage device that includes instructions that, when executed by processor circuitry in a system controller communicatively couplable to one or more control-source devices and one or more control-target devices operatively couplable to a respective one of one or more electrical load devices disposed in a space, causes the processor circuitry to:

receive data representative of an occupant within the space via a first communications interface circuitry communicatively couplable to a first network using a first network protocol;

receive, from a mobile device associated with the occupant of the space via second communications interface circuitry communicatively couplable to a second network using a second network protocol different from the first network protocol, data representative of:

one or more biometric parameters associated with the occupant in the space; and a unique identifier associated with the mobile device;

determine one or more output parameters for each of at least one of the one or more electrical load devices using the received unique identifier and the received data representative of the one or more biometric parameters associated with the occupant in the space; and communicate, via the first network using the first network protocol, the one or more determined output parameters to the control-target device associated with each respective one of the one or more electrical load devices.

24. The non-transitory, machine-readable, storage device of claim 23 wherein the instructions, when executed by the processor circuitry, further cause the processor circuitry to:

receive, from the mobile device, data indicative of initiation of an application on the mobile device via the second communications interface circuitry; and determine the one or more output parameters for each of the at least one of the one or more electrical load devices using:
the received data representative of the initiation of the application;
the received data representative of the one or more biometric parameters associated with the occupant in the space; and
the received unique identifier.

25. The non-transitory, machine-readable, storage device of claim 23 wherein the instructions, when executed by the processor circuitry, further cause the processor circuitry to:
receive data indicative of one or more medical conditions associated with the occupant of the space from a mobile device associated with the occupant via the second communications interface circuitry; and
determine the one or more output parameters for each of the at least one of the one or more electrical load devices using:
the received data representative of the one or more medical conditions of the occupant of the space;
the received data representative of the one or more biometric parameters associated with the occupant in the space; and
the received unique identifier.

26. The non-transitory, machine-readable, storage device of claim 25 wherein the instructions, when executed by the processor circuitry, further cause the processor circuitry to:
determine whether at least one of the one or more biometric parameters associated with the occupant of the space falls outside a predetermined range of allowable biometric parameter values based on the data representative of the one or more medical conditions associated with the occupant of the space;
determine one or more alert output parameters for each of at least one of the one or more electrical load devices responsive to the determination that at least one of the one or more biometric parameters associated with the occupant of the space falls outside the predetermined range of allowable biometric parameter values; and
communicate, via the first network, the one or more determined alert output parameters to the control-target device associated with each respective one of the one or more electrical load devices.

27. The non-transitory, machine-readable, storage device of claim 23 wherein the instructions that cause the processor circuitry to receive the data representative of one or more biometric parameters associated with the occupant in the space, further cause the processor circuitry to:
receive data indicative of one or more gestures by the occupant of the space.

28. The non-transitory, machine-readable, storage device of claim 27 wherein the instructions that cause the processor circuitry to receive data indicative of the one or more gestures by the occupant of the space, further cause the processor circuitry to:
receive, from at least one of the one or more control-source devices via the first communications interface circuitry, at least a portion of the data indicative of the one or more gestures by the occupant of the space.

29. The non-transitory, machine-readable, storage device of claim 27 wherein the instructions that cause the processor circuitry to receive data indicative of the one or more gestures by the occupant of the space, further cause the processor circuitry to:
receive, from the mobile device associated with the occupant of the space via the second communications interface circuitry, at least a portion of the data indicative of the one or more gestures by the occupant of the space.

30. The non-transitory, machine-readable, storage device of claim 23 wherein the instructions that cause the processor circuitry to determine the one or more output parameters for each of the at least one of the one or more electrical load devices using the received data representative of the one or more biometric parameters associated with the occupant in the space, further cause the processor circuitry to:
determine a respective output luminous intensity for each of one or more lamps using the received data representative of the one or more biometric parameters associated with the occupant in the space.

31. The non-transitory, machine-readable, storage device of claim 23 wherein the instructions that cause the processor circuitry to determine the one or more output parameters for each of the at least one of the one or more electrical load devices using the received data representative of the one or more biometric parameters associated with the occupant in the space, further cause the processor circuitry to:
determine a respective output color temperature for each of one or more lamps using the received data representative of the one or more biometric parameters associated with the occupant in the space.

32. The non-transitory, machine-readable, storage device of claim 23 wherein the instructions that cause the processor circuitry to determine the one or more output parameters for each of the at least one of the one or more electrical load devices using the received data representative of the one or more biometric parameters associated with the occupant in the space, further cause the processor circuitry to:
determine a respective output color spectrum for each of one or more lamps using the received data representative of the one or more biometric parameters associated with the occupant in the space.

33. The non-transitory, machine-readable, storage device of claim 23 wherein the instructions that cause the processor circuitry to determine the one or more output parameters for each of the at least one of the one or more electrical load devices using the received data representative of the one or more biometric parameters associated with the occupant in the space, further cause the processor circuitry to:
determine a respective output position for each of one or more motorized window coverings using the received data representative of the one or more biometric parameters associated with the occupant in the space.

* * * * *